(12) United States Patent
Roy et al.

(10) Patent No.: US 8,409,564 B2
(45) Date of Patent: Apr. 2, 2013

(54) RHODAMINE DERIVATIVES FOR PHOTODYNAMIC DIAGNOSIS AND TREATMENT

(75) Inventors: Denis-Claude Roy, Laval (CA); Martin Guimond, Columbus, OH (US); Nestor Molfino, Potomac, MD (US); Luc Villeneuve, Montreal (CA)

(73) Assignees: Universite de Montreal, Montreal (CA); Hopital Maisonneuve-Rosemont, Montreal (CA)

( * ) Notice: Subject to any disclaimer, the term of this patent is extended or adjusted under 35 U.S.C. 154(b) by 380 days.

(21) Appl. No.: 10/969,011

(22) Filed: Oct. 21, 2004

(65) Prior Publication Data

US 2006/0088507 A1 Apr. 27, 2006

Related U.S. Application Data

(63) Continuation of application No. 10/088,072, filed as application No. PCT/CA00/01142 on Oct. 3, 2000, now abandoned.

(60) Provisional application No. 60/157,790, filed on Oct. 5, 1999.

(51) Int. Cl.
*A61K 41/00* (2006.01)
*C07D 311/82* (2006.01)
*C12N 13/00* (2006.01)

(52) U.S. Cl. .................. 424/93.7; 549/227; 435/173.1

(58) Field of Classification Search ............... 424/93.7; 435/173.1; 549/227
See application file for complete search history.

(56) References Cited

U.S. PATENT DOCUMENTS

| | | | |
|---|---|---|---|
| 4,612,007 A | 9/1986 | Edelson | |
| 5,410,053 A * | 4/1995 | Hahn et al. | 546/48 |
| 5,556,992 A | 9/1996 | Gaboury et al. | |
| 5,773,460 A | 6/1998 | Gaboury et al. | |
| 5,798,523 A | 8/1998 | Villeneuve et al. | |
| 5,800,539 A | 9/1998 | Waller | |
| 5,871,946 A | 2/1999 | Lucas et al. | |
| 6,213,127 B1 | 4/2001 | Waller | |
| 2006/0252674 A1 | 11/2006 | Peritt et al. | |

FOREIGN PATENT DOCUMENTS

| | | |
|---|---|---|
| EP | 1 004 299 A1 | 5/2000 |
| WO | WO 90/03183 | 4/1990 |
| WO | WO 93/00005 | 1/1993 |
| WO | WO 96/07431 | 3/1996 |
| WO | WO 99/03976 | 1/1999 |

OTHER PUBLICATIONS

Darzynkiewicz et al. 1981. Increased mitochondrial uptake of rhodamine 123 during lymphocyte stimulation. PNAS 78:2383-2387.*

Pires et al. 1997. Ouabain Effects on Activated Lymphocytes: Augmentation of CD25 Expression on TPA-Stimulated Cells and of CD69 on PHA- and TPA-Stimulated Cells. Int. J. Immunopharmac., vol. 19, No. 3, pp. 143-148.*

Cuschieri. 1982. Cytochemical demonstration of increased adenosine triphosphatase activity in lymphocytes activated in vitro by phytohaemagglutinin or by the mixed lymphocyte reaction. Histochemical Journal 14, 139-148.*

Ferlini et al. Rhodamine 123: A Useful Probe for Monitoring T Cell Activation. cytometry 21:284-293 (1995).*

R.C. Nairn et al., "Rhodamine as a Fluorescent Probe of Lymphocyte Activation," *Immunology* (1979) vol. 36, pp. 235-240.

(Continued)

*Primary Examiner* — Taeyoon Kim
(74) *Attorney, Agent, or Firm* — O'Melveny & Myers LLP

(57) ABSTRACT

The present invention relates to the use of the photoactivable derivatives for the photodynamic treatment for the selective destruction and/or inactivation of immunologically reactive cells without affecting the normal cells and without causing systemic toxicity for the patient, wherein appropriate intracellular levels of said derivatives are achieved and irradiation of a suitable wavelength and intensity is applied.

2 Claims, 12 Drawing Sheets

OTHER PUBLICATIONS

Aldunate, J. et al., "*Trypanosoma cruzi*: trypanocidal effect of 2(3)-tert-butyl-4-hydroxyanisole (BHA) on several strains of epimiastigote and trypomastigote forms." Comparative Biochemistry and Physiology Part C: Comparative Pharmacology Toxicology 109C(2):119-127 (1994).
Carew J.S. et al., "Mitochondrial DNA mutations in primary leukemia cells after chemotherapy: clinical significance and therapeutic implications," Leukemia 17:1437-1447 (2003).
Chinnery, P.F., et al., "Accumulation of mitochondrial DNA mutations in ageing, cancer, and mitochondrial disease: is there a common mechanism?" The Lancet 360:1323-325 (Oct. 26, 2002).
Clayton, D.A., and Vinograd, J., "Complex Mitochondrial DNA in Leukemic and Normal Human Myeloid Cells," Proc. Nat'l. Acad. Sci. USA 62(4):1077-084 (1969).
Daniel, C. et al., "A Basis for Alloreactivity: MHC Helical Residues Broaden Peptide Recognition by the TCR," Immunity 8:543-552 (May 1998).
Guimond, M. et al., "Relapse after bone marrow transplantation: evidence for distinct immunological mechanisms between adult and paediatric populations," British Journal of Haematology 109: 130-137 (2000).
Klaesson, S. et al., "Immune Modulatory Effects of Immunoglobulins on Cell-Mediated Immune Responses In Vitro," Scand. J. Immunol. 38:477-84 (1993).
Polyak, K., et al., "Somatic mutations of the mitochondrial genome in human colorectal tumours," Nature Genetics 20:291-293 (Nov. 1998).
Spagnoli, G.C. et al., "Inhibitory Effects of Anit-HLA-A, B, C Heavy Chain and Anti-$\beta_2$ Microglobulin Monoclonal Antibodies on Alloantigen and Microbial Antigen-Induced Immune Response in Vitro," Scand. J. Immunol. 25:555-565 (1987).
Nairn, R.C. et al., "Rhodamine as a fluorescent probe of lymphocyte activation," Immunology 36:235-240 (1979).
Palathumpat, V. et al., "Induction of mixed lymphocyte reaction nonresponsiveness after chimeric thymus transplantation," Transplant Int 3:217-221 (1990).
Hamano, K., et al., "Prediction of Graft Prolongation by Mixed Lymphocyte Culture Following Anti-CD4 Monoclonal Antibody Treatment Among Different Donor-Recipient Combinations," Jpn J Surg 29:868-873 (1999).
Cohen et al. "CD4+CD25+ Immunoregulatory T Cells New Therapeutics for Graft-Versus-Host Disease." J. Exp Med. 196(3): 401-06, Abstract (Aug. 5, 2002).
Hori, S. et al. "Control of Regulatory T Cell Development by the Transcription Factor Foxp3." Science 299: 1057-61, 1057 (Feb. 14, 2003).
Mutis et al., "The association of CD25 expression on donor CD8+ and CD4+ T cells with graft-versus-host disease after donor lymphocyte infusions." Haematol 90(10): 1389-95, Abstract (Oct. 2005).
Sakaguchi, S. "Naturally Arising CD4+ Regulatory T Cells for Immunologic Self-Tolerance and Negative Control of Immune Responses." Annu. Rev. Immunol. 22: 531-62, Abstract (2004).
Truitt, R. et al. "Modification of T-Cells by a Psoralen and UVA for Stem Cell Transplantation: A Mouse Study." Abstracts of the 27th Annual Meeting of the American Society for Photobiology, Abstract No. TPM-B5, Photochem Photobiol 69 Suppl: 49S (Jun. 1999).
F. Adili et al., "Hemmung von allotranspantatabstossung nach photodynamischer therapie biologischer gefaessprothesen", Chirurgisches Forum Fuer Experimentelle Und Klinische Forschung, De Berlin, No. Suppl. 01, pp. 271-274, 1996.
M. Guimond (1) et al., "Specific elimination of anti-host T cell alloreactivity using a photodynamic approach" FASEB Journal. vol. 14, No. 6, p. A1074, Apr. 20, 2000.

N. Brasseur et al., "Eradication of multiiple myeloma and breast cancer cells by TH9402-mediate photodynamic therapy: implication for clinical ex vivo purging of autologous stem cell transplants" Photochem. Photobiol., 72(6), pp. 780-787, 2000.
Luc Villeneuve: "Ex vivo hotodynamic purging in chronic myelogenous leukemia and other noplasias with rhodamine derivatives" Biotechnol. Appl. Biochem., 30(1'), 1999.
F. Heshmati, et al.: "Extracorporeal photochemotherapy: a treatment for organ graft rejection", Therapeutic Pheresis, vol. 1, No. 2, pp. 121-125, 1997.
Cavazzana-Calvo M., et al., (1990) Transplantation, 50:1-7.
Tittle, T.V., et al. (1997) Blood 89-4652-58.
Harris, D.T., (1999) Bone Marrow Transplantation, 23:137-44.
Daniell, M.D., Hill, J.S. (1991) Aust. N.Z. Surg., 61:340-348.
Raab, O. (1990) Infusoria Z., Biol., 39:524-546.
Tappeiner, V.H. Jesionek A. (1903) Muench Med Wochneshr, 47:2042-2044.
Hausman W. (1911) Biochem Z., 30:276-316.
Dougherty, T.J. (1974) J. Natl. Cancer Inst., 51:1333-1336.
Dougherty, T.J. et al., (1975) J. Natl. Cancer Inst. 55:115-121.
Dougherty, T.J. et al., (1978) Cancer Research, 38:2628-2635.
Dougherty, T.J. (1984) Urol. Suppl., 23:61-64.
Dougherty, T.J. (1987) Photochem. Photobiol., 45:879-889.
Greinix, H.T., et al. Blood (1998) 92:3098-3104.
Hunt, D.W., et al. (1999) Immunopharmacology, 41:31-44.
Hryhorenko E.A., et al. (1998) Immunopharmacology, 40:231-40.
King. D.E. et al. (1999) Scand. J. Immunol. 49:184-92.
Zic. J.A., et al., Therapeutic Apheresis (1999)3:50-62.
Darzynkiewick. Z. Carter S. (1988) Cancer Research, 48:1295-1299.
Oseroff, A.R. (1992) In Photodynamic therapy (Henderson, B.W., Dougherty, T.J. eds.) New York:Marcel Dekker, pp. 79-91.
Bernal, S.D. et al., (1983) Science, 222:169-172.
Powers, S.K., et al. (1987) J. Neurosurg., 67:889-894.
Pilarski, L.M. (1995) American Journal of Hematology, 49:323-335.
Morliere, P., et al. (1990) Photochemistry and Photobiology, 52(4):703-710.
Chi-Wei Lin, (1990) In Photodynamic therapy of neoplastic disease. vol. II, CRC Press, pp. 79-101.
Albert, M.L. et al. Nature (1998) 392-86-89.
Lozzio, B.B. and Lozzio, C.B. (1979) Cancer Research, 3(6):363-370.
Roy, D.C., et al., JNCI (1996), 88:1136-1145.
Taswell C. The Journal of Immunology (1981) 126:1614-1619.
Graft-vs-Host Disease, Ferrara, J.L.M., Deeg, H.J., Burakoff, S.J. eds., Marcel Dekker, New York (1997).
Bone Marrow Transplantation, Forman. S.J. Blume K.G. Thomas, E.D., eds., Blackwell Scientific Publication, Cambridge, MA, USA, (1994).
Sullivan, K.M., et al., Am. Soc. Hematol., Educ. Program Book, (1998), 198-214.
Pal, Prabir et al., "Phototoxicity of some Bromine-Substituted Rhodamine Dyes: Synthesis, Photophysical Properties and Application as Photosensitizers", Photochem. Photobiol. (1996), 63(2), 161-8, XP-000979188.
Villeneuve, Luc: Ex vivo photodynamic purging in chronic myelogenous leukemia and other neoplasias with rhodamine derivatives:, Biotechnol. Appl. Biochem. (1999), 30(1), 1-17, XP000979118, p. 1.
Faseb Journal, (Apr. 20, 2000), vol. 14, No. 6, pp. A-1074-Abstract.
Christof, L., et al. (1998) British Journal of hematology, 101:722-727.
CAS Registry File, online, Apr. 12, 2004, pp. 1-4.

* cited by examiner

RESTING LYMPHOCYTES

ACTIVATED LYMPHOCYTES

RESTING LYMPHOCYTES

TIME (min) 70          90

ACTIVATED LYMPHOCYTES

RESTING LYMPHOCYTES

TIME (min)   110

ACTIVATED LYMPHOCYTES

1 - CONTROL, 0J/CM2
2 - CONTROL, 5J/CM2
3 - RH123 0J/CM2
4 - RH123 5J/CM2
5 - TH9402+RBBE, 0J/CM2
6 - TH9402+RBBE, 5J/CM2
7 - RBBE, 0J/CM2
8 - RBBE, 5J/CM2
9 - RBOE, 0J/CM2
10 - RBOE, 5J/CM2

RHODAMINE DERIVATIVES FOR PHOTODYNAMIC DIAGNOSIS AND TREATMENT

BACKGROUND OF THE INVENTION (a) Field of the Invention

The invention relates to a photodynamic treatment for the preferential destruction of immunologically reactive cells without substantially affecting the normal cells or causing systemic toxicity for the patient.

(b) Description of Prior Art

Immunologic disorders are conditions or diseases that result from the production of immune cells recognizing normal cells and tissues as foreign. Cells with immunoreactivity towards normal cells or tissues induce damages in these normal cells and tissues either directly, through cellular effector mechanisms, or indirectly through antibodies, cytokines or other mediators. Such immunologic disorders are usually divided in alloimmune conditions and autoimmune conditions. Alloimmune disorders occur primarily in the context of allogeneic transplantation (bone marrow and other organs: kidney, heart, liver, lung, etc.). In the setting of bone marrow transplantation, donor immune cells present in the hematopoietic stem cell graft react towards host normal tissues, causing graft-versus-host disease (GVHD). The GVHD induces damage primarily to the liver, skin, intestine, lung, eyes and mouth. Autoimmune disorders are comprised of a number of arthritic conditions, such as rhumatoid arthritis, scleroderma and lupus erythematosus; endocrine conditions, such as diabetes mellitus; neurologic conditions, such as multiple sclerosis and myasthenia gravis; gastrointestinal conditions, such as Crohn's disease and ulcerative colitis; hematological disorders, such as autoimmune hemolytic anemia, etc. The immune reaction in both alloimmune and autoimmune disorders progresses to generate organ dysfunction and damage.

Despite important advances in treatment, immunologic complications remain the primary cause of failure of allogeneic transplantations, whether in hematopoietic stem cell transplantation (GVHD) or in solid organ transplantation (graft rejection). In addition, autoimmune disorders represent a major cause of both morbidity and mortality. Prevention and treatment of these immune disorders has relied mainly on the use of immunosuppressive agents, monoclonal antibody-based therapies, radiation therapy, and more recently molecular inhibitors. Significant improvement in outcome has occurred with the continued development of combined modalities, but for a small number of disorders and patients. However, for the most frequent types of transplantation (bone marrow, kidney, liver, heart and lung), and for most immune disorders (rhumatoid arthritis, connective tissue diseases, multiple sclerosis, etc.) resolution of the immunologic dysfunction and cure has not been achieved. Therefore, the development of new approaches for the prevention and treatment of immunologic disorders is critically needed particularly for those patients who are at high risk or whose disease has progressed and are refractory to standard immunosuppressive therapy. Allogeneic stem cell transplantation (AlloSCT) has been employed for the treatment of a number of malignant and non-malignant conditions. Allogeneic stem cell transplantation is based on the administration of high-dose chemotherapy with or without total body irradiation to eliminate malignant cells, and host hematopoietic cells. Normal hematopoietic donor stem cells are then infused into the patient in order to replace the host hematopoietic system. AlloSCT has been shown to induce increased response rates when compared with standard therapeutic options. One important issue that needs to be stressed when using AlloSCT relates to the risk of reinfusing immune cells that will subsequently recognize patient cells as foreign and cause GVHD. A variety of techniques have been developed that can deplete up to 99,999% of T cells from the stem cell graft. These techniques, including immunologic and physical purging, are not entirely satisfactory. One major consideration when purging stem cell grafts is to preserve the non-host-reactive T cells so that they can exert anti-infectious and anti-leukemia activity upon grafting. The potential of photodynamic therapy, in association with photosensitizing molecules capable of destroying immunologically reactive cells while sparing normal donor-non-reactive immune cells to purge hematopoeitic cell grafts in the preparation of AlloSCT or autologous stem cell transplantation (AutoSCT) and after AlloSCT in the context of donor lymphocyte infusions to eliminate recurring leukemia cells has largely been unexplored. To achieve eradication of T cells, several approaches have been proposed including:

1) in vitro exposure of the graft to monoclonal antibodies and immunotoxins against antigens present on the surface of T cells (anti-CD3, anti-CD6, anti-CD8, etc.);
2) in vitro selection by soybean agglutinin and sheep red blood cell resetting;
3) positive selection of CD34+ stem cells with or without additional negative selection of T cells;
4) in vivo therapy with combinations of anti-thymocyte globulin, or monoclonal antibodies,
5) in vivo or ex vivo treatment with photosensitizing agents; and
6) In vitro or ex vivo exposure of recipient-reactive donor T cells by monoclonal antibodies or immunotoxins targeting the interleukin 2 receptor or OX-40 antigen (Cavazzana-Calvo M. et al. (1990) Transplantation, 50:1-7; Tittle T. V. et al (1997) Blood 89:4652-58; Harris D. T. et al. (1999) Bone Marrow Transplantation 23:137-44).

However, most of these methods are not specifically directed at the alloreactive T cell subset, but rather aiming at the elimination of either all T cells or broad T cell populations. This is associated with numerous problems, including disease recurrence, graft rejection, second malignancies and severe infections. In addition, the clinical relevance of several of these methods remains to be established.

There are many reports on the use of photodynamic therapy in the treatment of malignancies (Daniell M. D., Hill J. S. (1991) Aust. N. Z. *J. Surg.*, 61: 340-348). One of these uses is described in U.S. Pat. Nos. 5,556,992 and 5,773,460, where novel photoactivable rhodamine derivatives are used for the photodynamic therapy of a cancer patient by destroying human cancer cells, wherein appropriate intracellular levels of the derivatives are achieved and irradiation with light of a suitable wavelength is applied. The method has been applied for cancers of various origins and for the eradication of viruses and pathogens (Raab O. (1990) *Infusoria Z. Biol.*, 39: 524).

The initial experiments on the use of photodynamic therapy for cancer treatment using various naturally occurring or synthetically produced photoactivable substances were published early this century (Jesionek A., Tappeiner V. H. (1903) *Muench Med Wochneshr*, 47: 2042; Hausman W. (1911) *Biochem. Z.*, 30: 276). In the 40's and 60's, a variety of tumor types were subjected to photodynamic therapy both in vitro and in vivo (Kessel, David (1990) *Photodynamic Therapy of neoplastic disease*, Vol. I, II, CRC Press. David Kessel, Ed. ISBN 0-8493-5816-7 (v. 1), ISBN 0-8493-5817-5

(v. 2)). Dougherty et al. and others, in the 70's and 80's, systematically explored the potential of oncologic application of photodynamic therapy (Dougherty T. J. (1974) *J. Natl Cancer Inst.*, 51: 1333-1336; Dougherty T. J. et al. (1975) *J. Natl Cancer Inst.*, 55: 115-121; Dougherty T. J. et al. (1978) *Cancer Res.*, 38: 2628-2635; Dougherty T. J. (1984) *Urol. Suppl.*, 23: 61; Dougherty T. J. (1987) *Photochem. Photobiol.*, 45: 874-889). Several rhodamine derivatives were also found to display antitumor properties (U.S. Pat. Nos. 5,773, 460 and 5,556,992). The specificity of these photosensitizing agents for malignant cells, which demonstrate high proliferation rates, prompted us to evaluate these agents for the elimination of immunologic cells.

Treatment of Immunologic Cells with Photodynamic Therapy

There is currently a lack of agents, which allow selective destruction of immunologic cells while leaving intact the normal non-pathogenic residual cellular population. Preferential uptake of photosensitive dye and cytotoxicity of photodynamic therapy against lymphoid cells (Greinix H. T., et al. Blood (1998) 92:3098-3104; Hunt D. W. et al (1999) Immunopharmacology, 41:31-44; Heykorenko E. A et al (1998) Immunopharmacology 40: 231-40); and macrophages (Heykorenko E. A. et al (1998) Immunopharmacology 40: 231-40; King D. E. et al 1999) Scand J. Immunol 49: 184-92) cells have been previously demonstrated and reviewed in Zic J. A. et al. Therapeutic Apheresis (1999) 3:50-62.

It would be highly desirable to be provided with photosensitizers, which possess the following characteristics:
 i) preferential localization outside the nucleus and uptake by the immunologic cells;
 ii) upon application of appropriate light intensities, killing those cells which have accumulated and retained the photosensiting agents;
 iii) sparing a sufficient proportion of the normal hematopoietic stem cell compartment from the destructive effects of activated photosensitizers; and
 iv) potential utilization of photosensitizers for hematopoietic stem cell purging of immunologic cells in preparation for allogeneic or autologous stem cell transplantation.
 v) Potential utilization of photosensitizers for ex vivo elimination of cells of the immune system in patients with immunological disorders.

The Rhodamine Dyes

Rhodamine 123 (2-(6-amino-3-imino-3H-xanthen-9-yl) benzoic acid methyl ester)hydrochloride, a lipophilic cationic dye of the pyrylium class which can disrupt cellular homeostasis and be cytostatic or cytotoxic upon high concentration exposure and/or photodynamic therapy, although with a very poor quantum yield (Darzynkiewicz Z., Carter S. (1988) *Cancer Res.*, 48: 1295-1299). It has been used in vitro as a specific fluorescent stain for living mitochondria. It is taken up and is preferentially retained by many tumor cell types, impairing their proliferation and survival by altering membrane and mitochondrial function (Oseroff A. R. (1992) In *Photodynamic therapy* (Henderson B. W., Dougherty T. J., eds) New York: Marcel Dekker, pp. 79-91). In vivo, chemotherapy with rhodamine 123 can prolong the survival of cancerous mice, but, despite initial attemps to utilize rhodamine 123 in the treatment of tumors, the systemic toxicity may limit its usefulness (Bernal, S. D., et al. (1983) *Science*, 222: 169; Powers, S. K. et al. (1987) *J. Neurosur.*, 67: 889).

U.S. Pat. No. 4,612,007 issued on Sep. 16, 1986 in the name of Richard L. Edelson, discloses a method for externally treating human blood, with the objective of reducing the functioning lymphocyte population in the blood system of a human subject. The blood, withdrawn from the subject, is passed through an ultraviolet radiation field in the presence of a dissolved photoactive agent capable of forming photoadducts with lymphocytic-DNA. This method presents the following disadvantages and deficiencies. The procedure described is based on the utilization of known commercially available photoactive chemical agents for externally treating patient's blood, leaving immune cells from other sites intact in the process. According to Richard L. Edelson, the method only reduces, does not eradicate, the target cell population. This treatment strategy does not incorporate any attempt to enhance the immunoreactivity of target cells. Moreover, the wavelength range of UV radiation used in the process proposed by Richard L. Edelson could be damageable to the normal cells.

International Application published on Jan. 7, 1993 under International publication number WO 93/00005, discloses a method for inactivating pathogens in a body fluid while minimizing the adverse effects caused by the photosensitive agents. This method essentially consists of treating the cells in the presence of a photoactive agent under conditions that effect the destruction of the pathogen, and of preventing the treated cells from contacting additional extracellular protein for a predetermined period of time. This method concerned the eradication of infectious agents from collected blood and its components, prior to storage or transfusion, and does not impede on the present invention.

It would be highly desirable to be provided with a new use of rhodamine derivatives in the treatment of immunologic cells, which overcomes these drawbacks while having no substantial systemic toxicity for the patient.

SUMMARY OF THE INVENTION

One aim of the present invention is to provide new use of photosensitizers endowed with the following characteristics:
 i) preferential localization and uptake by the immunologic cells;
 ii) upon application of appropriate light intensities, functional or physical elimination of those cells which have accumulated and retained the photosensiting agents;
 iii) sparing a sufficient proportion of the normal hematopoietic T and stem cell compartment from the destructive effects of activated photosensitizers;
 iv) utilization of photosensitizers for hematopoietic stem cell purging of immunologic cells in preparation for allogeneic or autologous stem cell transplantation with or without the use of strategies to increase immunoreactivity; and
 v) utilization of photosensitizers for ex vivo elimination of reactive immune cells in patients with immunological disorders with or without the use of strategies.
 vi) utilization of photosensitizers to evaluate transport mechanism of immune and malignant cells.

In accordance with the present invention, there is provided a photoactivable pharmaceutical composition for the selective destruction and/or inactivation of immunologically reactive cells without substantially affecting the normal cells or causing systemic toxicity for the patient, the composition comprising at least one photoactivable rhodamine derivative selected from the group consisting of 4,5-dibromorhodamine 123 (2-(4,5-dibromo-6-amino-3-imino-3H-xanthen-9-yl)-benzoic acid methyl ester)hydrobromide; 4,5-dibromorhodamine 110 (2-(4,5-dibromo-6-amino-3-imino-3H-xanthen-9-yl)-benzoic acid)ethyl ester hydrobromide; 4,5-dibromorhodamine 110 (2-(4,5-dibromo-6-amino-3-imino-3H-xanthen-9-yl)-benzoic acid)octyl ester hydrobromide;

4,5-dibromorhodamine 110 (2-(4,5-dibromo-6-amino-3-imino-3H-xanthen-9-yl)-benzoic acid)n-butyl ester hydrobromide; Rhodamine B n-butyl ester (2-(6-diethyl amino-3-ethyl imino-3H-xanthen-9-yl)-benzoic acid)n-butyl diester hydrochloride; and photoactivable derivatives thereof; in association with a pharmaceutically acceptable carrier; whereby photoactivation of the derivatives induces cell killing while unactivated derivatives are substantially non-toxic to cells.

In accordance with the present invention, there is provided with the use of the photoactivable derivatives of the present invention for the photodynamic treatment for the selective destruction and/or inactivation of immunologically reactive cells without substantially affecting the normal cells or causing systemic toxicity for the patient, wherein appropriate intracellular levels of the derivatives are achieved and irradiation of a suitable wavelength and intensity is applied.

In accordance with the present invention, there is provided a method of prevention of graft-versus-host disease associated with allogeneic stem cell transplantation in a patient, which comprises the steps of:
 a) activating lymphocytes from a donor by mixing donor cells with host cells for a period of time sufficient for an immune reaction to occur;
 b) substantially eliminating the activated lymphocytes of step a) with photodynamic therapy using a therapeutic amount of a photoactivable composition of the present invention under irradiation of a suitable wavelength; and
 c) performing allogenic stem cell transplantation using the treated mix of step b).

In accordance with the present invention, there is provided a method for the treatment of immunologic disorder in a patient, which comprises the steps of:
 a) harvesting the patient's hematopoietic cells;
 b) ex vivo treating of the hematopoietic cells of step a) by photodynamic therapy using a therapeutic amount of a photoactivable composition of the present invention under irradiation of a suitable wavelength; and
 c) performing graft infusion or autograft transplantation using the treated hematopoietic cells of step b).

The method in accordance with a preferred embodiment of the present invention, wherein the immunologic disorder is selected from the group consisting of conditions in which self cells or donor cells react against host tissues or foreign targets, such as graft-versus-host disease, graft rejection, autoimmune disorders and immunoallergic conditions.

The method in accordance with a preferred embodiment of the present invention, wherein the hematopoietic cells is selected from the group consisting of bone marrow, peripheral blood, and cord blood mononuclear cells.

For the purpose of the present invention the following terms are defined below.

The term "immunologic disorders" is intended to mean any immunologic disorders such as alloimmune or autoimmune reaction and/or disorders.

The term "TH9402" is intended to mean 4,5-dibromorhodamine 123 hydrobromide salt.

The expression "preferential destruction of immunologically reactive cells without affecting substantially the normal cells or causing systemic toxicity for the patient." is intended to mean sparing a sufficient number of non-pathologic cells for a beneficial therapeutic effect.

The expression "photoactivable derivatives thereof" is intented to means substituted rhodamin 110 (2-(6-amino 3-imino 3H-xanthen-9-yl)benzoic acid) derivatives and their salts, which are activable by light. Preferred substituted rhodamine 110 derivatives include those comprising at least 1 and up to 8 halogen preferably bromine atoms substituents.

DETAILED DESCRIPTION OF THE INVENTION

Figure 1A:
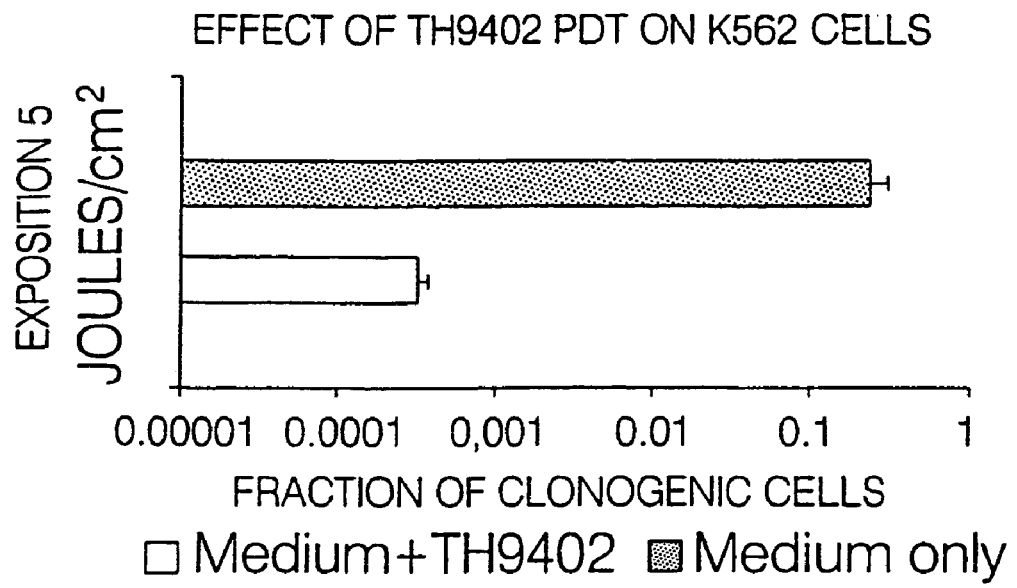
FIG. 1 is a graph of the phototoxicity of 4,5-dibromorhodamine 123 hydrobromide salt (TH9402) used in accordance with the method of the present invention against K562 and CEM cell lines admixed with normal irradiated PBMC and expressed as a fraction of the number of clonogenic cells.

Photoactive dyes are excited from the ground state to the singlet excited state following absorption of photons. Singlet excited states of organic molecules generally have short lifetimes ($10^{-12}$-$10^{-6}$ sec.) as they rapidly relax back to the ground state using non-radiative (vibrational modes) and radiative (fluorescence) processes. Intersystem crossing to the more stable triplet excited state is also competing with relaxation to the ground state. Triplet excited states generally have longer lifetimes ($10^{-6}$-10 sec) which allow them to diffuse and react with other molecules in the medium.

Triplet excited states can react with molecular oxygen via two different mechanisms. The first mechanism (Type I) consists of the transfer of an electron from the excited dyes to molecular oxygen, resulting in highly reactive free radical-anions being present in the cellular environment.

The second mechanism (Type II) consists of the transfer of energy from the excited dyes to molecular oxygen, leading to the formation of cytotoxic singlet oxygen.

Photosensitizers must therefore meet two conditions in order to be effective phototherapeutic agents. The first condition is that they must be present at a higher concentration in target cells than in normal cells. A higher concentration of dyes in malignant and immunologic cells results in a higher amount of photogenerated cytotoxic species and therefore in a higher death rate. The second condition is that irradiation of the phototherapeutic agent, in the presence of intracellular concentrations of molecular oxygen, must lead to the formation of the cytotoxic species with high efficiency.

Rhodamine 123 is known to be taken up and preferentially retained by many tumor cells and activated T cells and consequently its use as a phototherapeutic agent has been proposed. Intracellular rhodamine is also eliminated from cells by a channel transporter (Pgp-170) encoded for by the multiresistance gene (MDR-1). T cell activation leads to the inactivation of the Pgp-170 transporter, thus resulting in increased intracellular content of rhodamine (Pilarski L M (1995) Am. J. Hematol. 49: 323-35; Ludescher C (1998) Br. J. Haematol. 101: 722-7). However, the singlet excited state of Rhodamine 123 does not undergo intersystem crossing to the triplet excited state efficiently. Because of this, Rhodamine 123 is a weak photosensitizer (Morliere, P et al. (1990) *Photochemistry and Photobiology*, 52(4): 703-710).

To overcome the limitations of the prior art methods, the chemical structure of rhodamine 123 can be modified in a way to enhance intersystem crossing to the triplet excited state. Theoretically, this could be achieved by substituting heavy atoms, such as Br or other halides, for hydrogen atoms in the molecular structure of rhodamine 123. Therefore, dibromorhodamine 123 hydrobromide salt (referred herein as TH9402) has been prepared and tested.

The hydrophilicity properties of the amphipathic structure of the dyes could modulate the cytoplasmic and mitochondrial membranes and affect the phototoxicity of the dye. For example, hydrophobicity was shown to be the most important property influencing the in vitro uptake of porphyrins (Chi-Wei Lin (1990) *In Photodynamic therapy of neoplastic disease*, Vol II, CRC Press, pp 79-101). Therefore, different esters of rhodamine 123 and rhodamine B were prepared and tested. More specifically dibromorhodamine 110 n-butyl ester hydrobromide salt (DBBE) and rhodamine B n-butyl-ester hydrochloride salt (RBBE).

Different heavy atom substitutions of the hydrogen atoms (halogenic substitution) of the rhodamine backbone, for example, dibromo and diiodo derivatives of rhodamine B and rhodamine 110 esters, were prepared and tested.

Dimers/oligomers, hetero dimers/oligomers of such compounds could also be used if they demonstrate the appropriate cytotoxicity profile.

Substitution of the oxygen heteroatom of the rhodamine backbone by a heavier atom to reduce $S_0/S_1$ splitting, theoretically should increase spin orbit coupling and promote intersystem crossing from the $S_1$ to the $T_1$ state, producing higher triplet yields than the original dye. This should increase proportionally the production of singlet oxygen. Therefore, S (Sulfur), Se (Selenium) and Te (Tellurium) substitutions for the oxygen atom (O) of the rhodamine backbone is being explored.

Moreover, other strategies for increasing high quantum yields of Type I (free radical-anions) or Type II (singlet oxygen) products and tumor as well as activated immune cell selective accumulation of the dye are being tested.

Figure 3:
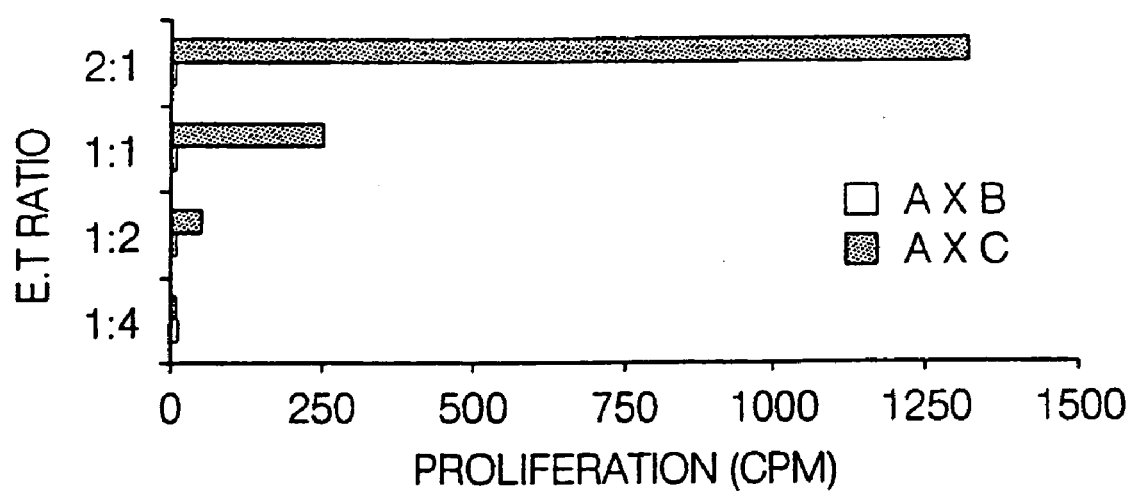
FIG. 3 demonstrates that cells from subject A activated against subject B cells and photodynamically treated, do not proliferate when reexposed to B cells but do proliferate when exposed to C cells. A, B and C cells were from unrelated individuals: A and B differed by 2 HLA antigens (B and DR).
Figure 4A:
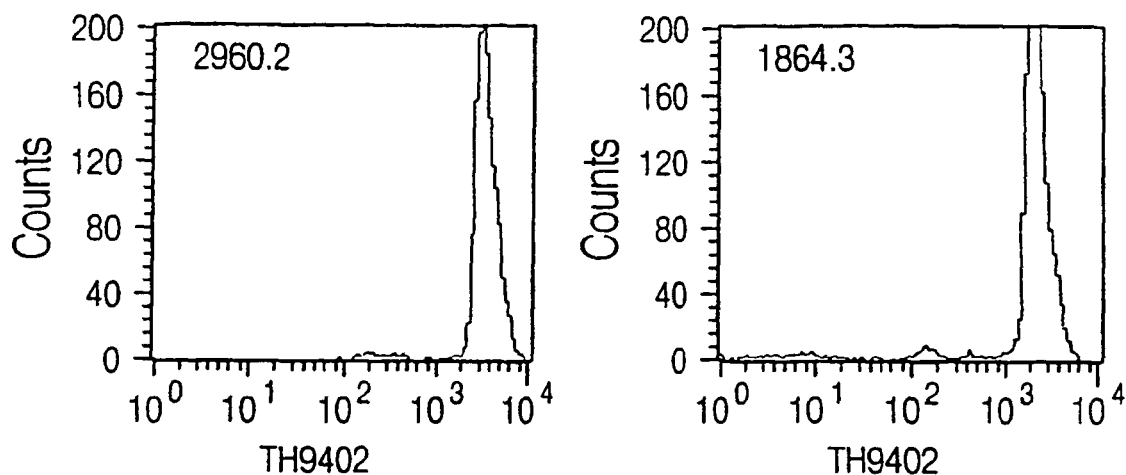
FIG. 4 shows TH9402 fluorescence upon flow cytometric evaluation of resting and activated lymphocytes. Cells were evaluated at various times after the end of the TH9402 incorporation period. Activated lymphocytes retain more TH9402 than resting lymphocytes.
Figure 4A:
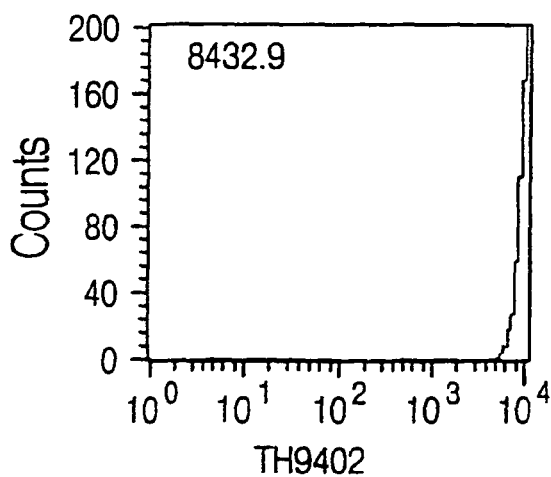
Figure 4A:
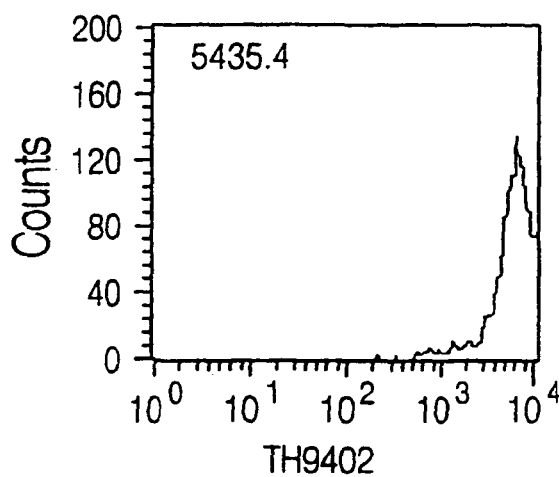
Figure 4B:
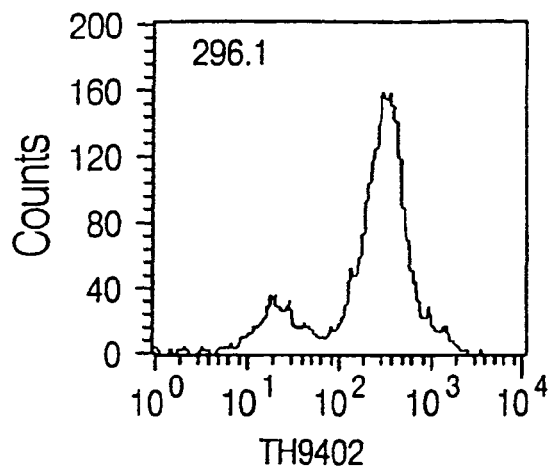
Figure 4B:
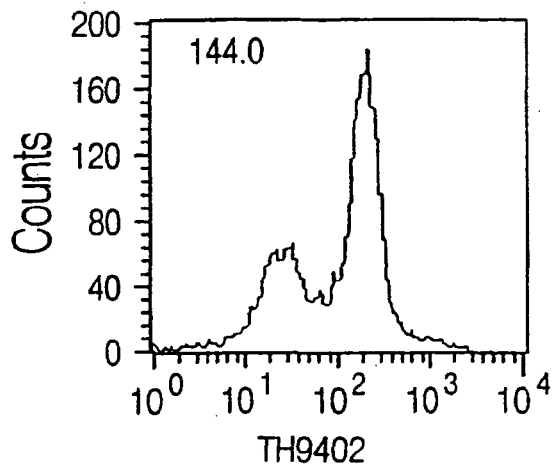
Figure 4B:
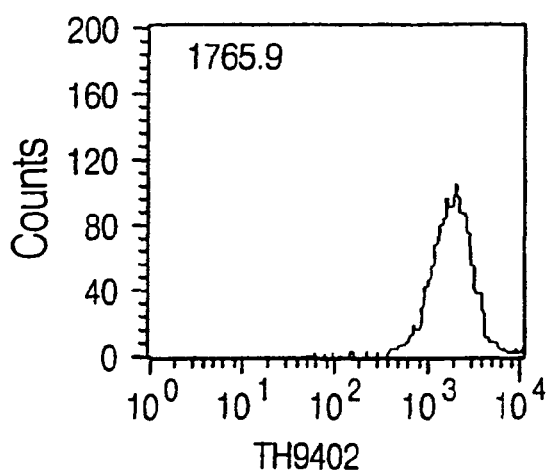
Figure 4B:
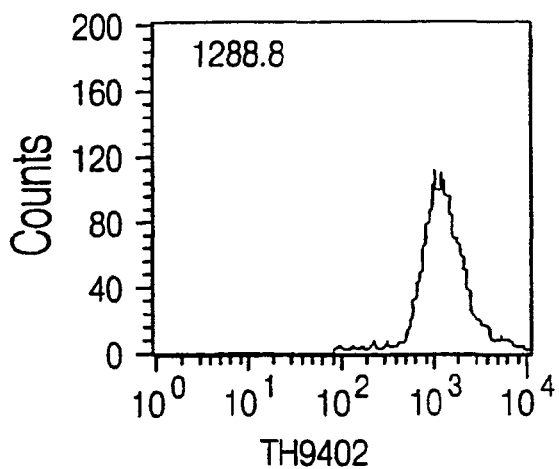
Figure 4C:
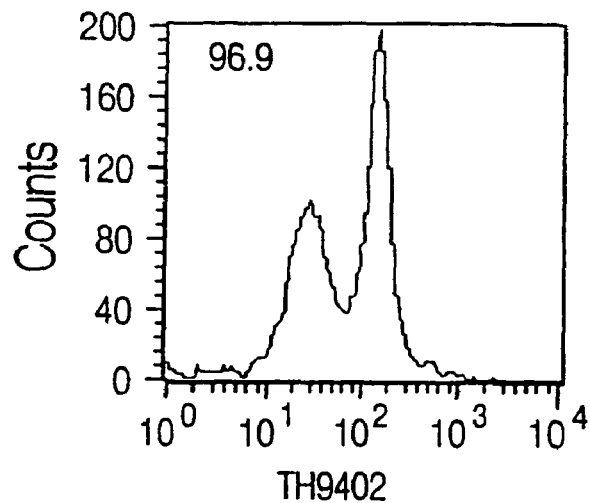
Figure 4C:
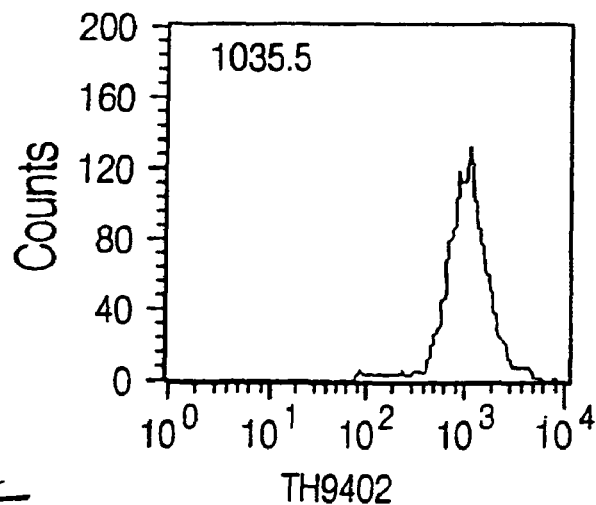
Figure 5:
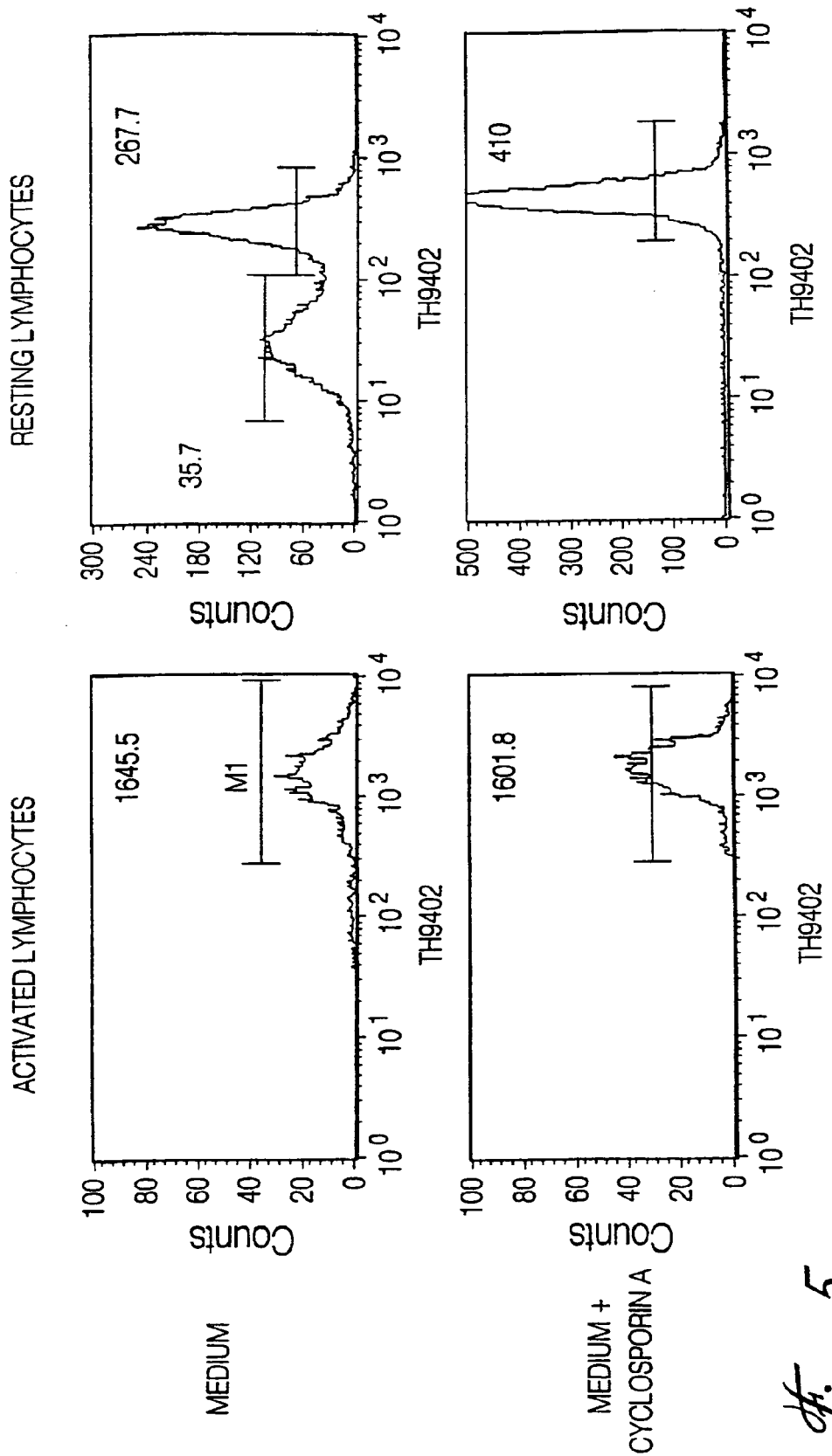
FIG. 5 shows the impact of cyclosporin A on the TH9402 cellular efflux after 110 minutes from the end of the TH9402 incorporation period. Cyclosporin A blocks the efflux of TH9402 in resting lymphocytes, but not in activated lymphocytes.

In accordance with the present invention, there is also shown that TH9402 is preferentially retained by activated T cells. Resting T cells can eliminate TH9402 from their intracellular milieu, but not activated T cells (FIG. 4). In addition, we found that TH9402 efflux is inhibited when cyclosporin-A is added (FIG. 5). Since cyclosporin-A is a potent inhibitor of Pgp-170, it is likely that TH9402 efflux relies on a Pgp-170 transporter, as previously observed for the rhodamine parent molecule. Inactivation of the MDR pathway in activated T cells could therefore explain the preferential elimination of activated T cells and preservation of unactivated T cells for subsequent recognition of third party cells (FIG. 3). The absence of known strong expression of Pgp-170 on B cells prompted us to evaluate the capacity of PDT with TH9402 to eliminate B lymphocytes. TH9402 was indeed found capable of eliminating approximately 3 logarithms (99.9%) of B lymphocytes. In contrast, more than half of normal hematopoietic progenitors of myeloid (CFU-GM), erythroid (BFU-E) and mixed (CFU-GEMM) origin are preserved when PDT is performed in the same conditions as used to obtain high levels of elimination of B lymphocytes. Therefore, PDT with TH9402 presents a therapeutic profile favorable to the elimination of immune cells, including activated T cells, B cells and potentially other cells (such as dendritic cells) that could be involved in immune disorders. The photodynamic treatment herein described could be done in conjunction with prior sensitization or activation of potential effector cells, or without manipulations to increase immunoreactivity since pathogenic immune cells may (1) be already activated because of the underlying disease, or (2) be spontaneously sensitive to PDT (e.g. B cells). Activation could be achieved through exposure to antigens, cells, cell lysates, proteins, peptides, DNA, cytokines, mitogens, lectins, or other directly or indirectly activating processes.

In accordance with the present invention, there is provided the use of such above-mentioned dyes in conjugation with antibodies specific for immune cell populations, peptides, proteins, or poisonous substances, or liposomal or lipoproteins, inhibitors of efflux pathways (e.g. MDR) or fluorochrome adducts or other agents.

In addition, the photosensitizers to be described have the potential to act synergistically in conjunction with other photoactive substances.

Moreover, the negative selection procedure provided by the use of photodynamic treatment does not preclude the use of other means for enriching hematopoietic stem cells such as positive selection with anti-CD34 monoclonal antibodies.

Clinical Applications

The first clinical application of the current invention is the use of photosensitizers in the context of in vitro purging of alloreactive cells prior to allogeneic stem cell transplantation for the prevention of graft-versus-host disease. In this condition, donor cells are first exposed to recipient cells or antigens or other components, in order to activate donor cells against antigens of the recipient. These cells then undergo photodynamic therapy to eliminate alloreactive donor cells. This strategy preserves hematopoietic cells that are non-reactive against host cells.

The same strategy (elimination of alloreactive cells from cellular grafts) could be applied in all instances where the administration of donor cells could induce graft-versus-host disease, such as in cases where donor lymphocytes are infused into recipients to exert anti-leukemia or anti-infection activity.

In the case of autoimmune disorders, a portion of immune cells are autoreactive. When autologous stem cell transplantation is performed to treat these disorders, the stem cell graft could contain immunoreactive cells leading to disease recurrence following transplantation. The photodynamic treatment described in this application could be used to eliminate immunoreactive cells from stem cell grafts prior to autologous transplantation.

In such immunologic disorders (both alloimmune and autoimmune), it would also be possible to use photodynamic therapy to eliminate cells involved in the immune disease process. Patient cells could be harvested by collecting peripheral blood or other cells or tissues, and photodynamically treated ex vivo to eliminate immunoreactive cells. After treatment, cells would be reinfused (1) to preserve the patient's pool of non-immunoreactive cells, (2) to create a favorable imbalance between immunoreactive and non-immunoreactive cells, and (3) to induce immunomodulation through enhanced presentation of antigens from immunoreactive cells, by injecting immunoreactive cells that will undergo apoptosis (Albert M. L. et al. Nature (1998) 392:86-9).

After its entry in cells, rhodamine is eliminated via transport mechanisms. Thus, rhodamine derivatives, including TH942, could be used to investigate mechanisms of cellular handling of such molecules. Interestingly, several agents, including chemotherapeutic agents, are eliminated through the same transport mechanisms as rhodamine. Measurement of such transport mechanisms with rhodamine derivatives, such as TH942, could be used to further our understanding of cellular and molecular biology, and could be used for diagnostic and prognostic purposes (e.g. identifying immunologically active cells or malignant cells that could be eliminated by chemotherapy, photodynamic or other therapeutic agents).

Chemical Synthesis

The chemical synthesis of rhodamine B n-buthylester hydrochloride, 4,5-dibromorhodamine n-butylester hydrobromide, rhodamine n-buthylester hydrochloride, 4,5-dibromorhodamine 110 n-butulester hydrobromide and 4,5-dibromorhodamine 123 hydrobromide was effected as described in U.S. Pat. No. 5,556,992 issued on Sep. 17, 1996, which is hereby incorporated by reference.

Cell Lines

T cells represent the most important population of immune cells present in the peripheral blood. In order to demonstrate the efficacy of photodynamic therapy with TH9402 to eliminate activated T cells, we first evaluated its effect on a malignant T cell line. Phototoxicity was also evaluated in parallel against the chronic myelogenous leukemia cell line K562, that had been used in U.S. Pat. Nos. 5,556,992 and 5,773,460. The CEM T cell acute lymphoblastic leukemia cell line and K562 chronic myelogeneous leukemia cell line (Lozzio, B. B. and Lozzio, C. B. (1979) *Cancer Res.*, 3(6): 363-370) were obtained from the American Type Culture Collection (ATCC, 12301 Parklawn Drive, Rockville, Md. 20852 USA) under the accession number CCL-119 and CCL-243. Cultures were maintained at 37° C. in a humidified incubator with an atmosphere of 95% air and 5% $CO_2$. Cells were grown in RPMI 1640 medium (GIBCO, Grand Island, N.Y.)) supplemented with 10% fetal bovine serum (FBS), 2 mM L-glutamine, 1 mM sodium pyruvate, 100 U/mL penicillin, and 100 μg/mL streptomycin (Life Technologies, Inc.). Before each experiment, cell viability was assessed by trypan blue exclusion. CEM or K562 cells were admixed with normal irradiated mononuclear peripheral blood cells in a 1:1 ratio and then underwent photodynamic treatment. Before being mixed with CEM or K562 cells, normal PBMC received 25 Gy of radiation at 4 Gy/minute ($^{137}$Cs; Gamma Cell, Atomic Energy of Canada, Ottawa, ON).

Photodynamic Treatment

Suspensions of cells were then incubated with 10 μM TH9402 for 40 minutes at 37° C. Cells were treated at $1\times10^6$ cells/mL in X-vivo-15 medium without phenol red (BioWhittaker, Walkersville, Md., USA) supplemented with 2.5% FBS. At the end of the incubation period, cells were spun down and the cell pellet resuspended in the X-vivo culture medium in the absence of dye, supplemented with 10% FBS. Cells were then placed in T-flasks (Corning, Cambridge, Mass., USA) for 90 minutes at 37° C. Following this second incubation in medium without dye, cells were exposed at 3 mm thickness to desired light energy, usually 5 joules/cm² using a previously described light delivery device (U.S. Pat. No. 5,798,523). Light energy was delivered using a fluorescent scanning lamp device with maximum wavelength around 512 nm.

Phototoxicity of 4,5-dibromorhodamine 123 hydrobromide (TH9402)

Figure 1B:
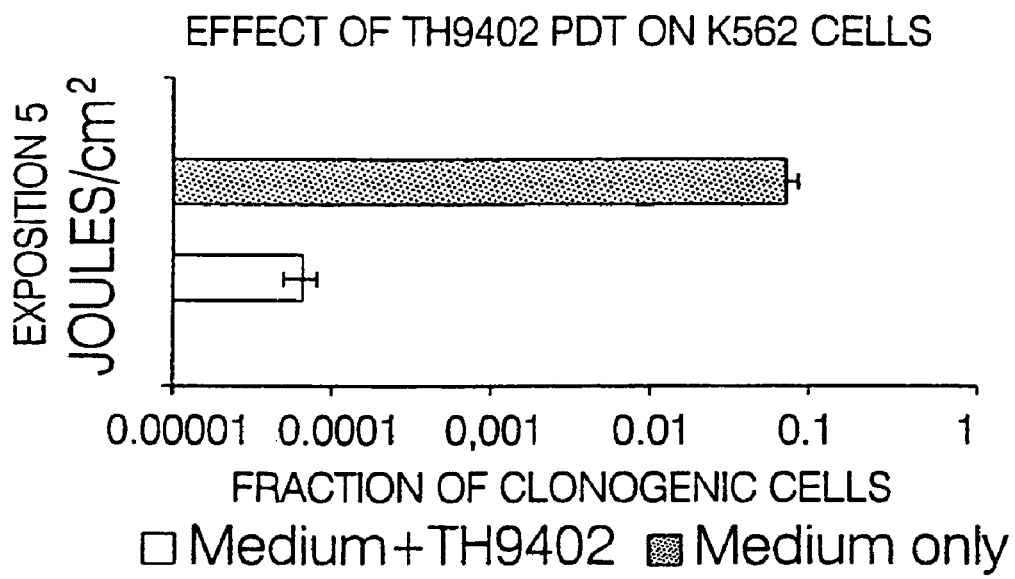

To assess the photochemotherapeutic potential and the in vitro phototoxicity of 4,5-dibromorhodamine 123 hydrobromide (TH9402), the T cell line CEM and the leukemic line K562 admixed with normal irradiated PBMC were incubated with TH9402 and exposed to 5 joules/cm² of light (as described above). After photodynamic treatment, cells were washed 3 times and plated in a limiting dilution assay (LDA) as described previously (Roy D C et al, *JNCI* 1996; 88:1136-45). Briefly, each treatment sample was serially diluted from $5\times10^5$ to 0.5 cells per 100 μl in RPMI 1640 supplemented with 10% FBS. Then, 24 aliquots of each dilution were plated in flat bottom microculture plates (Nunclon, Nunc, Denmark). Cells were fed every 4 days and incubated at 37° C. for 12-14 days. Growth at each serial dilution was assessed in an "all-or-nothing" (positive or negative) fashion under an inverted phase microscope. Frequency of clonogenic cells within the test population was estimated using chi-square minimization (Taswell C, *J. Immunol.* 1981; 126:1614-19). As shown in FIG. 1, photodynamic therapy with TH9402 eliminated almost all CEM and K562 cells, with less than 0.1% of CEM and K562 escaping elimination by phototherapy in comparison to the media only sample. These results indicate high levels of elimination of malignant T cells, as was previously reported for leukemic K562 cells, and support efficacy of this procedure for the elimination of malignant T cells. TH9402 was shown to be highly phototoxic; the elevated level of cytotoxic activity is believed to be a consequence of increased intracellular content of TH9402 in these malignant T and myeloid cell lines.

T Cell Activation with PHA.

Normal PBMC were activated by incubation at 37° C. for 48 to 72 hours in X-vivo-15 medium (Biowhittaker, Walkersville. Md. U.S.A.) supplemented with 20% AB serum (Sigma), 1% pen-strep (Gibco), 2% glutamin (Gibco) and 20 μg/ml of phytohemagglutinin-A (PHA-P) (Sigma). Cells were cultured in 25 cm² flasks at a concentration of $3\times10^6$ cells/ml. Following incubation, cells were washed and treated with the TH9402 photodynamic treatment as described above, and proliferative activity measured as described below.

Proliferation Assay (Mixed Lymphocyte Reaction)

To evaluate the residual proliferative potential of activated mononuclear cells after photodynamic therapy, peripheral blood mononuclear cells were placed in 96-well microtiter plates and were incubated with PBMC from various individuals (demonstrating at least 2 major histocompatibility complex antigen mismatches with treated cells). The latter cells were serially diluted in order to obtain effector (treated cells) to target ratios ranging from 2:1 to 1:4 ($4 \times 10^4$ treated effector cells/well) and incubated at 37° C. for 5 days. Eighteen hours prior to harvesting, 1 µCi of $^3$H-thymidine was added. Cells were harvested using a PHD cell harvester (Cambridge Technology, Boston, Mass., USA). Radioactivity in the cell harvest was counted using a liquid scintillation counter (Beckman, Chicago, Ill., USA).

Figure 2:
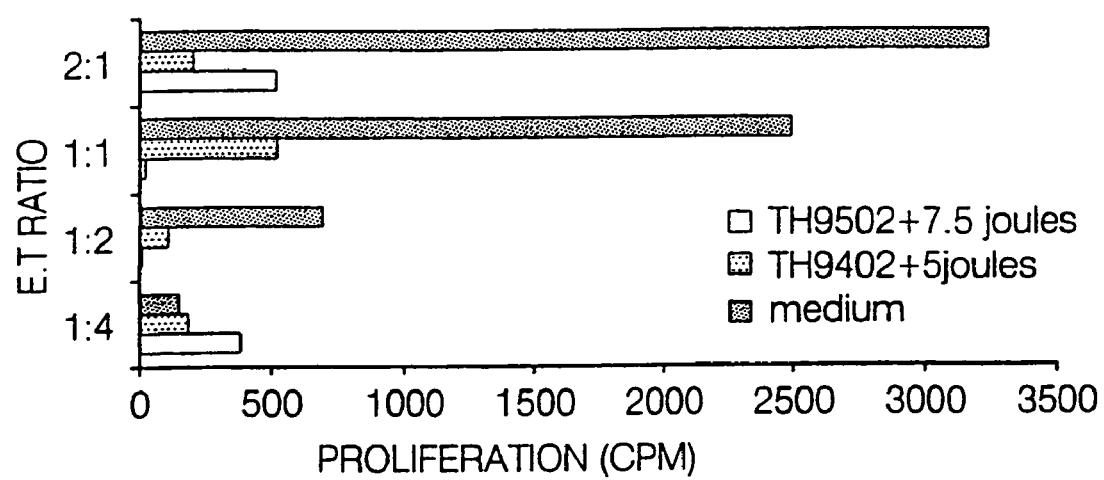
FIG. 2 demonstrates that PHA activated lymphocytes stop incorporating 3H-thymidine after photodynamic therapy with 7.5 and 5 joules/cm$^2$, in contrast to medium treated cells.

Phototoxicity of 4,5-dibromorhodamine 123 hydrobromide Against PHA Activated Cells The phototoxicity of TH9402 against PHA-activated PB mononuclear cells was assessed after photodynamic treatment using 5 and 7.5 joules/cm$^2$ of light energy (FIG. 2). After treatment, the cells were washed and evaluated for proliferative activity in a mixed lymphocyte reaction, according to the protocol in the previous paragraph. In PHA-activated cells that did not receive photodynamic therapy (untreated), proliferation in mixed lymphocyte culture increased with the number of effector cells. In contrast, when PHA-activated cells were treated with TH9402 using 5 and 7.5 J/cm$^2$ light energies, reactivity towards MHC incompatible cells was abrogated. This result indicates that photodynamic therapy of PHA-activated cells is a very potent inhibitor of immunoreactivity in these cells. Cell counts performed three days after the photodynamic treatment show a decrease by more than ninety percent (90%) of the treated cells in comparison to the medium control. These results indicate that the loss of proliferative activity in activated cells is most likely due to the elimination of effector cells.

Allogeneic T Cell Activation

Another appproach was used in this study to activate cells against specific target antigens. Mononuclear cells from subject A were incubated with irradiated mononuclear cells from subject B. In this one-way mixed lymphocyte culture, subjects A and B were unrelated and showed only partial human leukocyte antigen (HLA) matching with differences at two major histocompatibility complex (MHC) antigens. Briefly, $25 \times 10^6$ PBMC were incubated at 37° C. for 4 days with $25 \times 10^6$ irradiated (25 Gy) stimulating mononuclear cells in X-vivo-15 medium (BioWhittaker) supplemented with 20% AB serum (Sigma), 1% pen-strep (Gibco), 2% glutamin (Gibco) and 50 U/ml of IL-2 (ID lab). All cultures were performed in 75 cm$^2$ flasks (Corning) in a final volume of 25 ml. The unstimulated control was performed with $25 \times 10^6$ irradiated autologous cells.

After this activation period, cells had photodynamic therapy with TH9402 as described above. Following treatment, cells were plated in a proliferation assay for 5 days as described above where targets consisted of PBMC from subject B and also from subject C (mismatched unrelated). As shown in FIG. 3, when cells from subject A, activated against B, underwent TH9402 photodynamic therapy, they did not proliferate when reexposed to cells from B. However, when the same A cells were exposed to C cells, they had retained the capacity to proliferate. These results indicate that photodynamic therapy can specifically eliminate alloreactive cells, while sparing the alloreactive potential of unactivated cells. In addition, they demonstrate that it is possible to take advantage of this activation strategy to deplete immunologic populations against a desired antigen.

Cellular Concentration of TH9402

TH9402 cellular content in resting and activated lymphocytes was evaluated by flow-cytometry, since the intensity of TH9402 (green) fluorescence correlates with the cellular content in TH9402. Briefly, $10^6$ cells/ml, previously activated or not with PHA, were incubated in X-vivo-15 medium supplemented with 2.5% human AB serum and 10 µM TH9402 for 40 minutes. These cells were washed two times with X-vivo medium supplemented with 10% AB serum and cells analysed by flow cytometry 30, 50, 70, 90 and 110 min after the end of the TH9402 incorporation period. As shown in FIG. 4, resting lymphocytes rapidly lost TH9402 with approximately 50% (fifty percent) of cells demonstrating low TH9402 fluorescence 110 minutes after the end of the incorporation period. In addition, at all time-points evaluated, the intensity of TH9402 fluorescence was less for resting lymphocytes than for activated lymphocytes (FIG. 4). Since cellular concentration of TH9402 correlates with the extent of cell elimination, the high concentration of TH9402 maintained in activated lymphocytes explains their sensitivity to photodynamic therapy. In contrast, the rapid efflux of TH9402 from resting lymphocytes should explain preservation of their proliferative activity.

In order to identify the mechanism responsible for the differential retention of TH9402 between activated and resting lymphocytes, cyclosporin-A was used to block the multidrug transporter (P-gp 170). These cells were incubated with 10 µM TH9402 for 8 minutes, and washed with medium containing 1 µg/ml cyclosporin-A or medium alone. TH9402 retention was subsequently evaluated by flow-cytometry (green fluorescence) (FIG. 5). After 110 minutes from the end of TH9402 incorporation, fluorescence intensity was identical in activated cells treated or not treated with cyclosporin A. In contrast, cyclosporin A induced higher retention of TH9402 in resting lymphocytes, suggesting that a functional P-gp is involved in TH9402 dye efflux from resting lymphocytes and represents a major mechanism whereby these cells escape elimination by photodynamic therapy. The functional impairment of such a pump in activated lymphocytes could explain the high levels of phototoxicity observed in these cells.

Phenotypic Analysis of Residual T Lymphocytes After Phototherapy Using TH9402

In order to determine if the abrogation of reactivity toward subject B obtained after PDT correlated with the loss of activated T cells, the proportion of activated cells was determined in samples exposed or not to PDT. Activated cells can be discriminated from resting T lymphocytes by their enhanced expression of CD25, which can be detected with a monoclonal antibody specific for CD25, the inducible a chain of the IL-2 receptor. Briefly, after activation of T cells in mixed lymphocyte reaction, as described above, activated T lymphocytes were incubated in X-vivo 15 medium (BioWhittaker) supplemented with 2.5% human AB serum and 10 µM TH9402 for 40 min. These cells were than washed twice with X-vivo-15 medium supplemented with 10% AB human serum. At 110 min after the end of the incubation period, cells were exposed to doses of light ranging from 2.5 to 10 joules/cm$^2$ of using the above described light delivery device (U.S. Pat. No. 5,798,523). Light energy was delivered using a fluorescent scanning device with maximum wavelength at 512 nm. After treatment, cells were cultured for 48 to 72 hours in X-vivo-15 medium supplemented with 15% of human AB serum. After the latter incubation period, cells were counted and their immunophenotypes analyzed by dual-color flow cytometry to determine the proportion of activated T lymphocytes. Monoclonal antibodies consisted of anti-CD4-APC, -CD8-APC and -CD25-PE with appropriate isotypic controls (Coulter Immunology, Hialeah Fla.). Flow-cytometric analysis was performed using conventional protocols (Roy D. C. et al. (1996) J.N.C.I. 88:1136-45).

Figure 6:
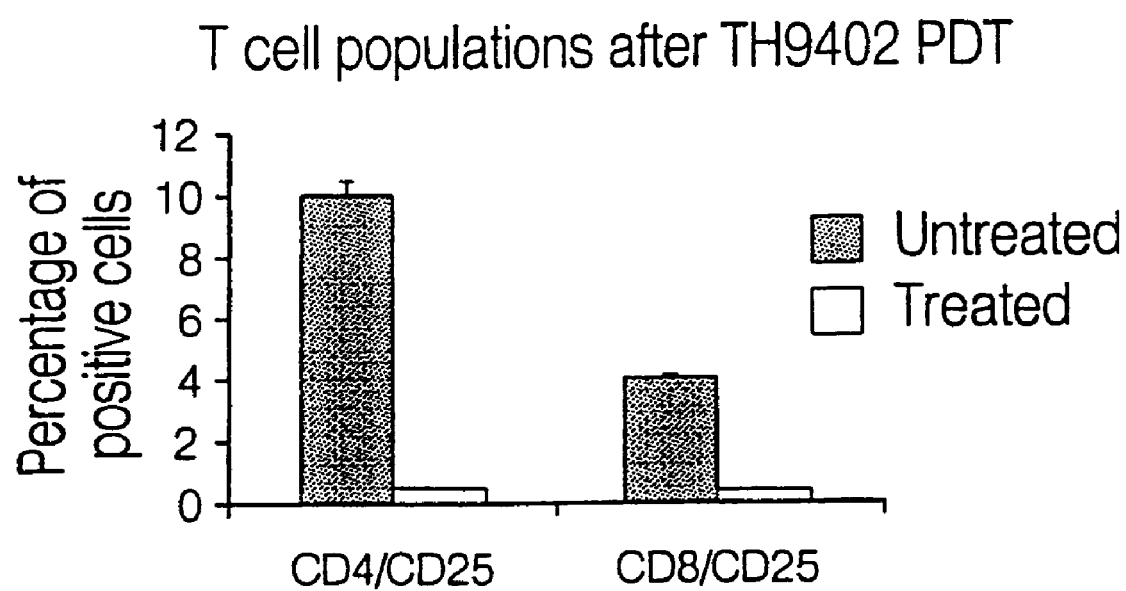
FIG. 6 shows the effect of PDT with TH9402 on CD4 and CD8 positive cells after activation in mixed lymphocyte culture with third party cells. Activated cells (expressing CD25), both CD4+ and CD8+, are eliminated by photodynamic therapy.

In the cells not treated by PDP, activated T lymphocytes represented 14% of the total lymphocyte population (CD8 and CD4) (FIG. 6). FIG. 6 shows that the activated cells (expressing CD25), both CD4+ and CD8+, are eliminated by photodynamic therapy. In contrast, the proportion of activated T lymphocytes, both CD4+ and CD8+ was below 1% for cells exposed to all light intensities in this experiment (2.5., 5 and 10 joules/m$^2$). These results confirm the capacity of PDT with TH9402 to eliminate activated T cells.

Differential Phototoxic Activity of TH9402 Against B Cells and Non-Lymphoid Hematopoietic Progenitors To evaluate the potential of PDT with TH9402 to eliminate other immune cell populations, normal human B cells were used as targets. Mononuclear cells from normal donors were obtained by leukopheresis, and resuspended at 20 million cells per ml during the whole PDT process. Cells were centrifuged and resuspended in pre-warmed (37° C.) X-Vivo-15 medium supplemented with 2.5% FCS and 10 U/ml heparin, with 5 µM TH9402. After 40 minutes of incubation at 37° C., cells were washed and resuspended in a X-Vivo-15 medium and 10% FCS with 10 U/ml heparin (medium free of TH9402) for an efflux period of 50 minutes before exposure to light energy (10 to 30 Joules/cm$^2$). Cells underwent light exposure at 20 million cells per ml and at a thickness of 2 cm.

To evaluate the capacity of the PDP treatment to eliminate B cells, we used an in vitro B cell culture system. Briefly, $5 \times 10^6$ untreated and treated mononuclear cells were added to a 25 mm$^2$ monolayer of irradiated mouse fibroblasts NIH 3T3 transfected to express CD40 ligand, an important molecule for B cells activation and proliferation. The cells were cultured during seven days in interleukin-4 (IL-4) (100 u/ml) containing-medium (Iscove's Modified Dulbecco Medium-1 MDM) with 2% FCS, 1% penicillin-streptomycin, 50 µg/ml human transferrin, 0.5% BSA, 5 µg/ml bovine insulin, 50 µg/ml of each oleic, linoleic and palmitic acid). At the end of the culture period, a trypan blue viability test was done as well as an immunophenotypic analysis of residual CD19+ cells by flow-cytometry as described above.

To verify that the treatment preserved normal hematopoetic progenitors, we have used a clonogenic assay to measure the amount of hematopoetic clonogenic precursors present in the same samples. Briefly, after PDP, all samples, including controls, were diluted and plated at various cells densities (10,000 to 800,000) cells in semi-solid methylcellulose medium (StemCell Technologies Inc). Colonies were enumerated for myeloid, erythroid, and mixed progenitors after 13 to 16 days of incubation at 37° C., 5% CO$_2$ and 98% relative humidity. Assays were done at least in duplicate. To determine the comparative reduction of the precursor cells, the mean values for each PDP condition were converted to percent of the appropriate control.

Figure 7A:
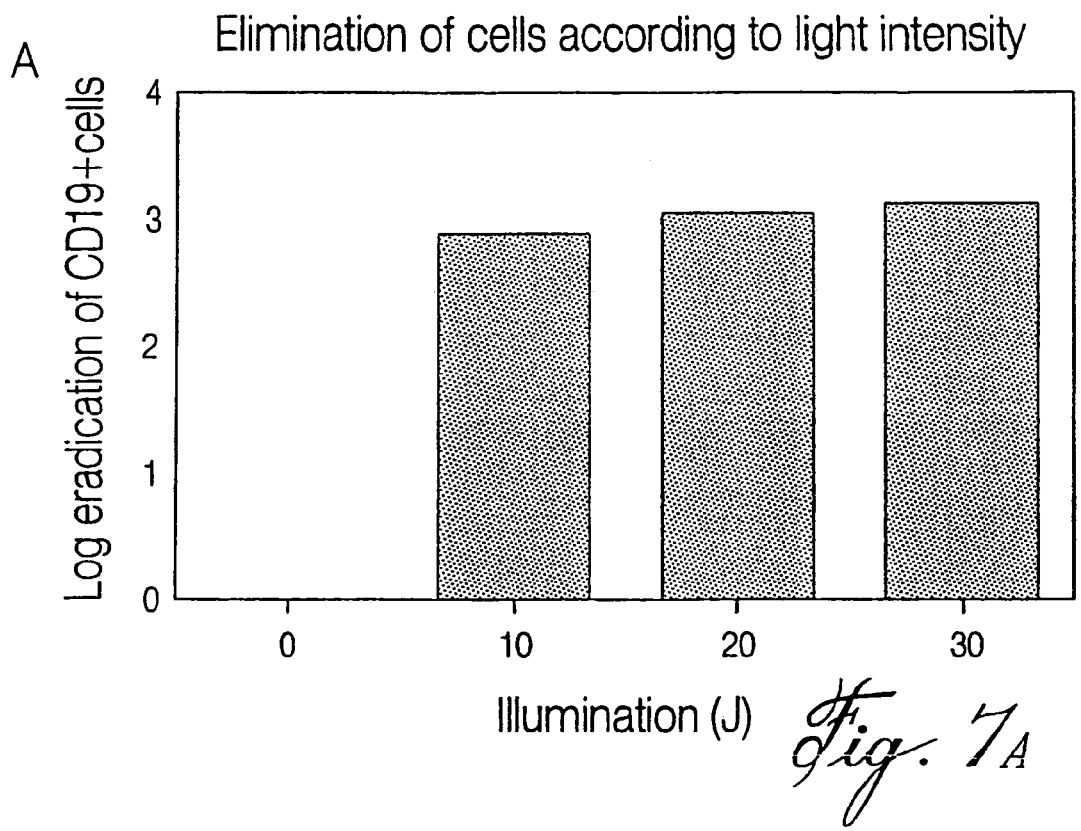
FIGS. 7A and 7B show that approximately 3 logarithms (99.9%) of human B cells can be eliminated by PDT with TF9402 (A). In contrast, less than one logarithm (approximately 50%) of hematopoietic progenitor cells of myeloid (colony forming units-granulocyte monocyte [CFU-GM], erythroid (burst forming units-erythroid [BFU-E], and mixed (colony forming units-granulocyte erythrocyte monocyte megakaryocyte [CFU-GEMM]) origin are eliminated by the same PDT procedure.
Figure 7B:
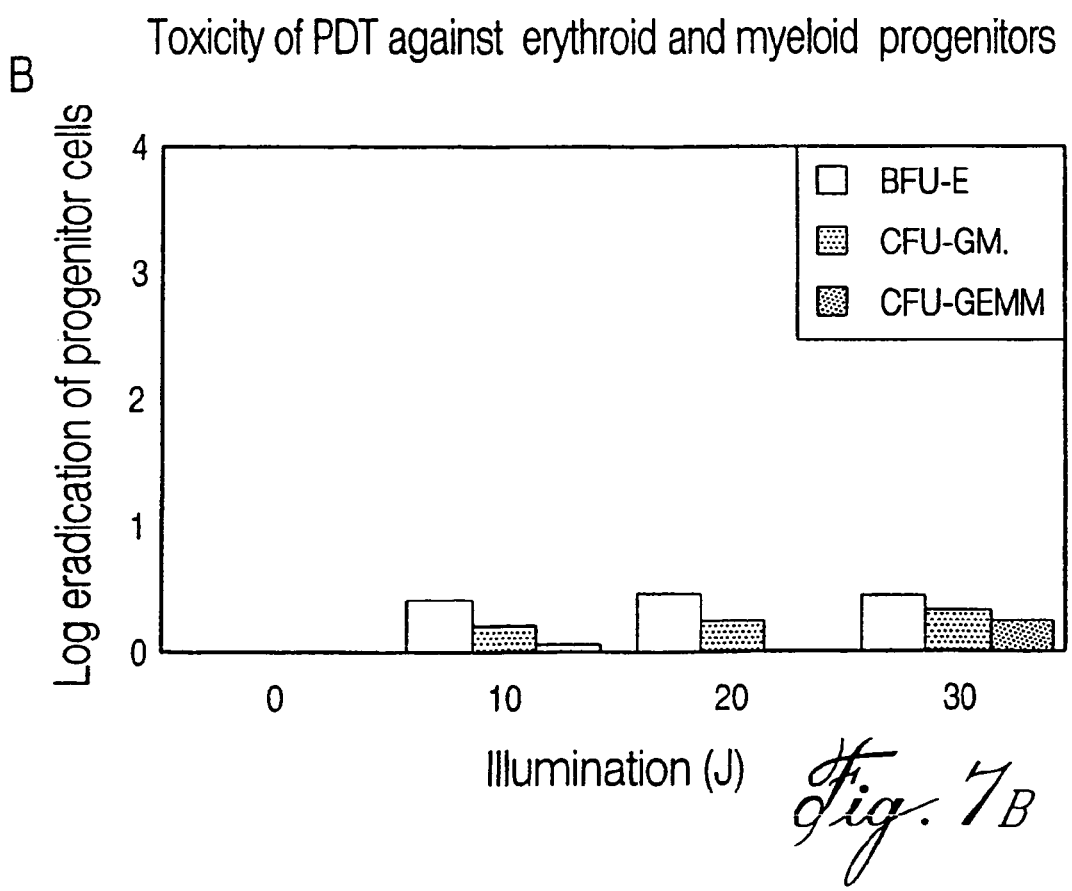

Normal human mononuclear cells were obtained and subjected to various PDP conditions to determine the efficacy of eradication of B cells, specificity and safety of the procedure. The number of B cells eliminated by TH9402 PDT increased with the level of light energy delivered (FIG. 7A). In comparison to untreated cells, PDT resulted in approximately 3 logarithms (99.9%) of eradication of B cells. In contrast, when these cells were evaluated for the elimination of non-lymphoid hematopoietic progenitors, usually less than 50% (half of a logarithm) of these progenitors were eliminated by the same conditions of PDT (FIG. 7B). These results indicate that immune cells other than activated T cells, such as B cells, can be eliminated by PDT with TH9402. In addition, preservation of a large proportion of CFU-GM, BFU-E and CFU-GEMM progenitors demonstrates the specificity of this PDT process for defined immune cell populations. In addition, it confirms the capacity of such PDT to preserve normal hematopoietic progenitor cells for hematologic reconstitution when used in the context of purging of grafts prior to autologous or allogeneic transplantation.

Phototoxicity of 4,5-dibromorhodamine 110 n-butyl ester hydrobromide

Figure 8A:
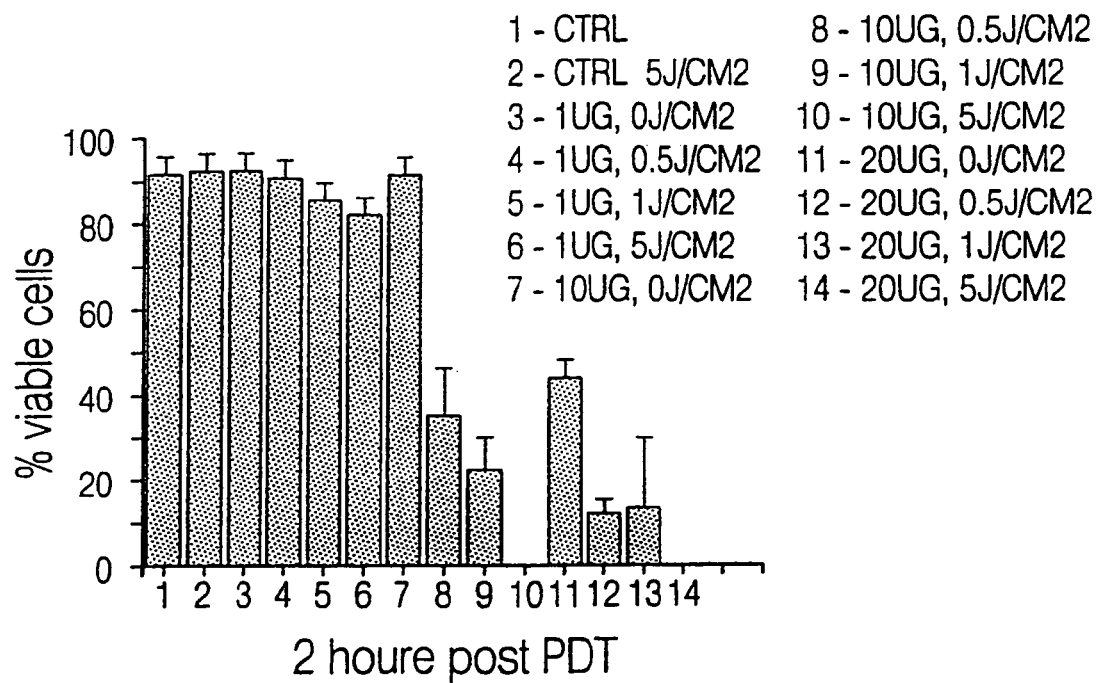
FIGS. 8A, 8B, and 8C show three graphs of the photo toxicity of 4,5-dibromorhodamine 110 n-butyl ester hydrobromide salt used in accordance with the method of the present invention and expressed in % viability.
Figure 8B:
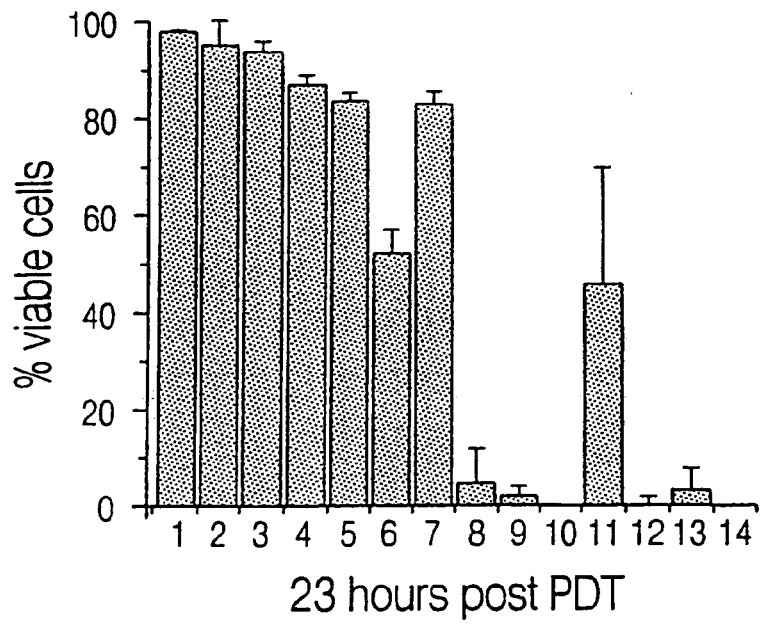
Figure 8C:
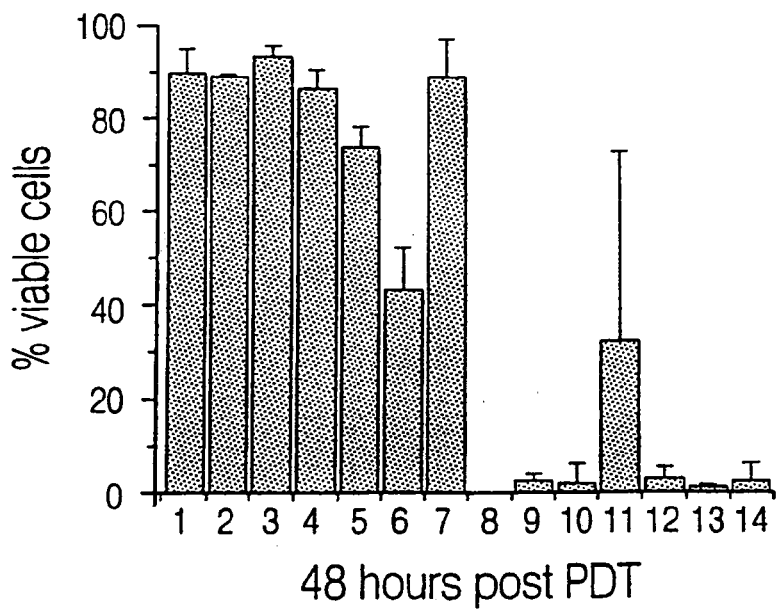

To ascertain the photochemotherapeutic potential of 4,5-dibromorhodamine 110 n-butyl ester hydrobromide (DBBE), in vitro phototoxicity was evaluated in the K-562 cell line procedure described. The cells were incubated with increasing concentrations of DBBE and the cell viability was measured at different time points following photodynamic therapy. The results shown in FIGS. 8A, 8B and 8C show that a dosage of 10 µg/ml of the dye and a brief exposure to 514.5 nm radiation from an argon ion laser at 0.5 J/cm$^2$ completely suppress cell viability in less than 24 hours after irradiation.

Phototoxicity of Rhodamine B n-butyl ester hydrochloride

Figure 9A:
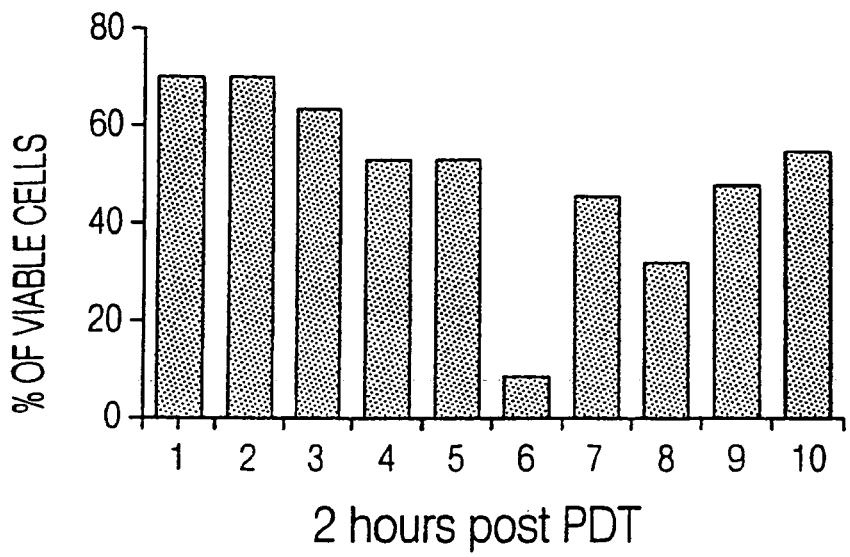
FIGS. 9A and 9B show two graphs of the photo toxicity of rhodamine B n-butyl ester hydrochloride salt used in accordance with the method of the present invention and expressed in % viability.
Figure 9B:
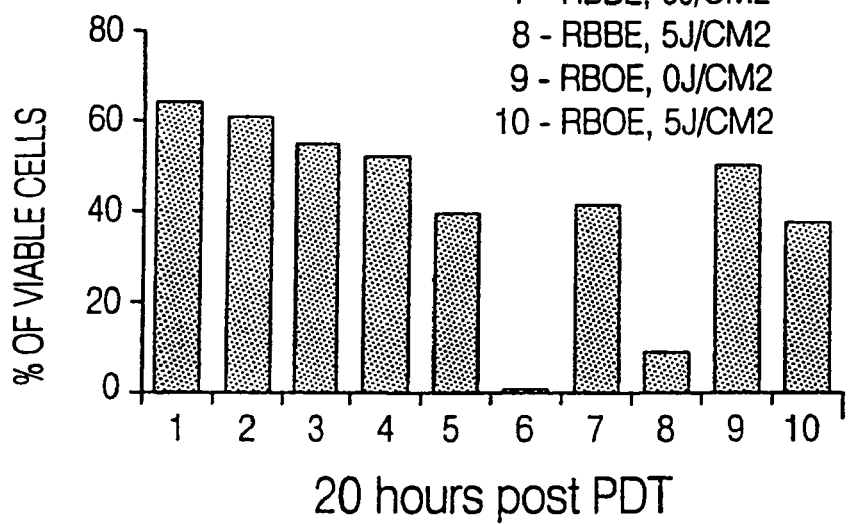

The photo toxicity in vitro of rhodamine B n-butyl ester (RBBE) was evaluated in the K-562 cell line procedure, in order to assess its photochemotherapeutic potential. Comparison was made to the induced phototoxicity of rhodamine 123 (RH123) and of rhodamine nB-butyl ester hydrochloride. Cell viability was evaluated 2 and 20 hours after photodynamic therapy. The results shown in FIGS. 9A and 9B demonstrate that a dosage of 10 µg/ml of the dye and a photo exposure of 5 J/cm$^2$ from argon ion laser (514.5 nm) significantly suppress cell viablity of K562 cells in less than 20 hours after irradiation. Rhodamine 123 has no effect on cell viability, even at exposures of 5 J/cm$^2$. Phototoxicity of 4,5-dibromorhodamine 110 n-butyl ester hydrobromide and rhodamine B n-butyl ester hydrochloride were only assessed against the cell line K562. However, we anticipate that their activity will be similar against T cells.

Photoxicitity Against Hematopoietic Progenitor Cell Cultures

It is observed that the photo treatment alone, at energy levels up to 10 J/cm2, or the pre-incubation of the cells at saturating concentrations of the dyes did not affect neither the establishment of the long term culture nor the formation in semi solid assays of cellular colonies issued from the multiplication and differentiation of committed progenitors present in the bone marrow (colony forming units-erythrocytes (CFU-E), blast forming units-erythrocytes (BFU-E), colony forming units-granulocytes, macrophages, (CFU-G-M)). However, as reported for rhodamine 123, the LTC (Long Term Culture) establisment is more sensitive to the dyes but the number of viable commited precursor and stem cells remains unaffected. Photodynamic therapy with rhodamine 123, rhodamine B n-butyl ester hydrochloride and 4,5-dibromorhodamine 110 n-butyl ester hydrobromide minimally impaired the establishment of normal mouse long term culture of bone marrow and the formation of hematopoietic colonies in semi-solid assays. This is in agreement with results obtained previously in other laboratories using rhodamine 123.

Conventional approaches for the prevention and treatment of immunologic disorders such as immunosuppressive agents, radiotherapy and monoclonal antibody-based therapies are limited by their intrinsic toxicity and myelosuppressive effects. The introduction of strategies to eliminate T cells in vitro or in vivo has resulted in a decreased incidence of graft-versus-host disease after allogeneic stem cell transplantation, improved graft survival in solid organ transplantation and improved clinical conditions for patients with immunologic disorders. However, T cell depletion is associated with an increased incidence of infections and malignancies or recurrence of malignant diseases, which have limited the use of T cell elimination strategies. These complications are primarily attributable to the non-specific elimination of a majority of T cells, which are responsible for the control of infection and anti-leukemia activity. To overcome these limitations and to expand the number of patients and age limit for intensive curative therapy, the potential benefit of selective in vitro elimination of immunologic cells prior to allogeneic stem cell transplantation has become widely acknowledged. Moreover, selective elimination of immunologic cells has the potential to be most useful in the context of donor lymphocyte infusion after transplantation, solid organ transplantation, and autoimmune disorders where the patient might benefit from the elimination of alloreactive or activated immune cell populations.

In an effort to develop new anti-neoplastic drugs that would allow selective destruction of alloreactive or activated immune cells, new dye molecules have been prepared and tested as possible new photosensitizers, useful for the photodynamic prevention and therapy of immunologic disorders. Three new photosensitizers of the pyrylium family were prepared and their cytotoxicity profile, which is similar to that of TH9402, provides evidence for their potential use in the photodynamic treatment of immunologic disorders and also in the prevention and/or treatment of graft-versus-host disease.

The present invention will be more readily understood by referring to the following examples which are given to illustrate the invention rather than to limit its scope.

Example I

Method of Prevention of Graft-Versus-Host Disease in the Context of Allogeneic Stem Cell Transplantation Diagnosis and Identification of Immunological Differences Between Donor and Recipient, and Graft-Versus-Host Disease:

Allogeneic stem cell transplantation is performed for numerous neoplastic and non-neoplastic conditions. Hematological malignancies are comprised of leukemia, lymphoma, multiple myeloma, myelodysplastic syndromes, etc.; and non-hematological malignancies: aplastic anemia, congenital disorders, severe immunodeficiency syndromes, rhumatoid arthritis, scleroderma, lupus erythematosus, multiple sclerosis, HIV and other immune disorders.

Graft-versus-host disease is a complication of allogeneic stem cell transplantation, where donor cells react against host cells, damaging target tissues (usually skin, liver, gut, lung, lacrymal or salivary glands, etc.). The diagnosis relies on several clinical and laboratory parameters, that are extensively reviewed in *Graft-vs.-Host Disease*, Ferrara J L M, Deeg H J, Burakoff S J eds, Marcel Dekker, New York, 1997.

GVHD develops against antigens present on recipient cells but not on donor cells. Immunological differences between donor and recipient could be present at the level of major histocompatibility antigens, minor histocompatibility antigens or tumor-associated antigens. Disparity is established using one or more of the following procedures on blood or bone marrow cells:
  a) HLA typing: conventional serologic typing or molecular to identify disparities between donor and recipient in major histocompatibility complex class I and class II antigens; and
  b) Mixed lymphocyte culture to identify differences in class II antigens; and
  c) Minor histocompatibility antigens: although a few cytotoxic T cell lines are available and could be used to identify minor histocompatibility antigens, currently, these tests are only available for research purposes.

Progenitor Cell Harvesting

After diagnosis, bone marrow (BM) or peripheral blood (PB) or cord-blood derived hematopoietic stem cells from the donor is harvested using previously described procedures for allogeneic progenitor cell transplantation (reviewed in Bone Marrow Transplantation, Forman S J, Blume K G, Thomas E D eds, Blackwell Scientific Publications, Cambridge Mass., USA, 1994). Donor hematopoietic stem cells collected for allografting can be immediately incubated with irradiated (25Gy) host mononuclear or other cells. Host cells admixed with donor cells are incubated in sterile dye free medium supplemented with 20% autologous serum and interleukin-2 for 2 to 5 days. This procedure elicits donor cell alloreactivity towards the host, and the cell graft subsequently undergoes photodynamic treatment ex vivo as described below.

Selective in vitro Purging of Immunologic Cells

Ex vivo treatment consist of short-term incubation of previously activated BM or PB stem cells with one or several of the selected photoactive compounds. Duration of incubation, cell concentration and drug molarity is determined for each patient using an aliquot of the harvested cell population. Excess of dyes is removed by cell washes with sterile dye free medium supplemented with 2% autologous serum. Cells are next being exposed to radiant energy of sufficient intensities to effect photodynamic purging of immune cells. Efficacy of the photodynamic purging procedure is verified on an aliquot of the treated cell population, before cryopreservation and/or re-infusion to the patient is performed. Until re-infusion to the patient, the cells can be cryopreserved in 10% dimethylsulfoxyde (DMSO) and 90% autologous serum, at −196° C. in the vapor phase of liquid nitrogen.

Systemic Treatment of Patients

Following stem cell harvest, the patient is submitted to dose-intensive chemotherapy and/or irradiation when indicated.

Allogeneic Stem Cell Transplantation

Following appropriate treatment of the patient by high-dose chemotherapy and/or irradiation and at the appropriate clinical moment, cryopreserved marrow or peripheral blood or cord blood stem cells will be rapidly thawed and returned to the patient.

Example II

Method of Treatment of Graft-Versus-Host Disease and Autoimmune Diseases

Diagnostic Procedures

Diagnosis of graft-versus-host disease or immunologic disorders is established using conventional clinical, biochemical and/or histopathological examination of the blood or appropriate tissues. Diagnostic and predictive features of GVHD are reviewed in *Graft-vs.-Host Disease*, Ferrara J L M, Deeg H J, Burakoff S J eds, Marcel Dekker, New York, 1997.

Harvesting of Peripheral Blood Cells

After diagnosis of severe GVHD, autoimmune or immunologic disorder, peripheral blood (PB) mononuclear cells are harvested using previously described or similar leukopheresis procedures (reviewed in *Bone Marrow Transplantation*, Forman S J, Blume K G, Thomas E D eds, Blackwell Scientific Publications, Cambridge Mass., USA, 1994). Patient's peripheral blood mononuclear cells collected are treated immediately ex vivo as described below.

In vitro Elimination of Cells Mediating GVHD

Ex vivo treatment consists of short-term incubation of PB mononuclear cells with one or several of the selected photoactive compounds. Duration of incubation, cell concentration and drug molarity are determined for each patient using an aliquot of the harvested cell population. Excess of dyes is removed by cell washes in sterile dye free medium supplemented with 2% autologous serum. Cells are next being exposed to radiant energy of sufficient intensities to effect photodynamic purging of activated cells which mediate GVHD.

Administration of Photodynamically Treated Cells to Patients

Leukopheresed cells that are photodynamically treated are reinfused into the patient. This approach enables the elimination of a large number of circulating activated lymphocytes and other cells involved in GVHD. In addition, cells spared by the photodynamic treatment are unactivated and their reinfusion into the patient may help restore normal immunologic equilibrium and induce immunomodulation.

Example III

Method of Treatment of Immunologic Disorders

Diagnostic Procedures

Diagnosis of autoimmune disorders is established using conventional clinical, biochemical and/or histopathological examination of the blood or appropriate tissues. Severe autoimmune diseases are amenable to autologous transplantation (reviewed in Sullivan K M et al., *Am. Soc. Hematol.*, Educ. Program Book, 1998: 198-214).

Harvesting of Hematopoietic Stem Cells

After diagnosis, bone marrow (BM), peripheral blood (PB) or cord blood (CB) mononuclear cells are harvested using previously described procedures for the autologous marrow transplantation in cancer therapy (reviewed in *Bone Marrow Transplantation*, Forman S J, Blume K G, Thomas E D eds, Blackwell Scientific Publications, Cambridge Mass., USA, 1994). Patient's hematopoietic stem cells collected for autograft are treated immediately ex vivo as described below.

In vitro Elimination of Cells Mediating Autoimmune Disorders

Ex vivo treatment consists of short-term incubation of BM or PB stem cells with one or several of the selected photoactive compounds. Duration of incubation, cell concentration and drug molarity is determined for each patient using an aliquot of the harvested cell population. Excess of dyes is removed by cell washes in sterile dye free medium supplemented with 2% autologous serum. Cells are next being exposed to radiant energy of sufficient intensities to effect photodynamic purging of immunologic cells which mediate the immunologic disorder.

Administration of Photodynamically Treated Cells to Patients

Hematopoietic stem cells that are photodynamically treated are stored (frozen or kept in culture). This approach enables the elimination of a large number of activated lymphocytes and other cells involved in the immunologic disorder. In addition, cells spared by the photodynamic treatment are unactivated and their reinfusion may help restore normal immunologic equilibrium. Following stem cell harvest, patient are either treated with conventional regimens until autografting is clinically indicated or immediately submitted to dose-intensive chemotherapy and total body irradiation where indicated.

Autologous Stem Cell Transplantation

Following high-dose chemotherapy and irradiation cryopreserved marrow or peripheral blood stem cells are rapidly thawed and infused to the patient.

Example IV

Method of Identification of Membrane Transporters

Diagnosis of autoimmune and neoplastic disorders is established using conventional clinical, biochemical and/or histopathological examination of the blood or appropriate tissues.

In vitro Evaluation of rhodamine Derivative Transporters (MDR-Related and Non-Related)

Peripheral blood or bone marrow cells from patients with autoimmune or cancer cells is incubated with one or several of the selected photoactive compounds. Duration of incubation, cell concentration and drug molarity will be determined for each type of cell evaluated. Excess dye wil be removed by cell washes with and without agents interfering with the cellular elimination of rhodamine derivatives, such as cyclosporin-A, verapamil or probenecid among others. These agents will be introduced in sterile dye free medium supplemented with 2% autologous serum. Cells will next be exposed to flow-cytometric evaluation (light energy) of adequate wavelength and sufficient intensity to effect fluorescence of rhodamine derivatives in targeted cells. Cells that spontaneoulsy eliminate photoactive compounds harbor multidrug receptor (MDR)-related or other transporters. The addition of blocking agents (such as cyclosporin-A or verapamil) will prevent the elimination of photoactive compounds and confirm the presence of functional MDR-related or other transporters on cells.

Conclusion

Rhodamine derivatives enable the study of these specific transporters, in basic, translational and clinical studies. This is useful for the investigation of cellular and molecular biology. Because MDR and other similar transporters can limit the activity or various therapeutic agents such as chemotherapeutic and photodynamic agents, this test should have diagnostic and prognostic importance and help identify optimum therapeutic strategies for patients with immunologic and neoplastic disorders.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method of reducing or preventing graft-versus-host disease associated with allogeneic stem cell transplantation, which comprises the steps of:
   a) harvesting hematopoietic cells from a patient with an immunologic disorder;
   b) harvesting hematopoietic cells from a donor;
   c) mixing the cells of step a) with the cells of step b) ex vivo for a period of time sufficient to activate lymphocytes within the hematopoietic cells harvested from said donor such that an immune reaction occurs, wherein an activated portion and an unactivated portion is produced;

d) adding to the mixture of cells of step c) ex vivo a therapeutic amount of a rhodamine derivative according to formula (I):

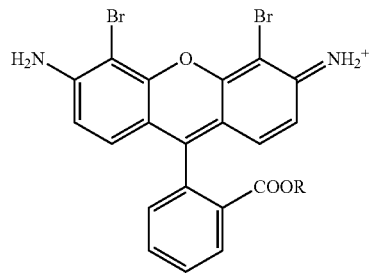

wherein R=methyl, ethyl, octyl or n-butyl;

e) irradiating the mixture of cells of step d) ex vivo with a suitable wavelength and intensity for the selective destruction and/or inactivation of the activated portion without substantially affecting the unactivated portion or causing systemic toxicity in said patient; and f) infusing the mixture of cells of step e) into the patient.

2. The method of claim 1, wherein said rhodamine derivative is of the formula (II):

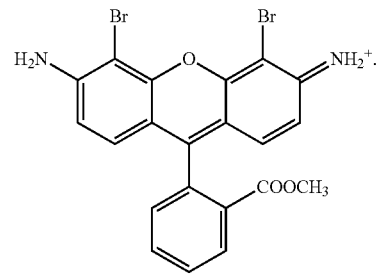

* * * * *